US008580801B2

(12) United States Patent
Henkin

(10) Patent No.: US 8,580,801 B2
(45) Date of Patent: Nov. 12, 2013

(54) PHOSPHODIESTERASE INHIBITOR TREATMENT

(76) Inventor: Robert I. Henkin, Bethesda, MD (US)

( * ) Notice: Subject to any disclaimer, the term of this patent is extended or adjusted under 35 U.S.C. 154(b) by 500 days.

(21) Appl. No.: 12/508,530

(22) Filed: Jul. 23, 2009

(65) Prior Publication Data

US 2010/0022563 A1 Jan. 28, 2010

Related U.S. Application Data

(60) Provisional application No. 61/083,147, filed on Jul. 23, 2008.

(51) Int. Cl.
*A01N 43/90* (2006.01)
*A01N 43/42* (2006.01)
*A61K 31/522* (2006.01)
*A61K 31/47* (2006.01)

(52) U.S. Cl.
USPC ..................................... 514/263.34; 514/312

(58) Field of Classification Search
USPC ............................................ 514/263.34, 312
See application file for complete search history.

(56) References Cited

U.S. PATENT DOCUMENTS

| | | | |
|---|---|---|---|
| 174,915 | A | 3/1876 | Lorenz |
| 4,066,405 | A | 1/1978 | Henkin |
| 4,146,501 | A | 3/1979 | Henkin |
| 4,652,521 | A | 3/1987 | Confer et al. |
| 4,683,195 | A | 7/1987 | Mullis et al. |
| 4,683,202 | A | 7/1987 | Mullis et al. |
| 4,800,159 | A | 1/1989 | Mullis et al. |
| 4,992,445 | A | 2/1991 | Lawter et al. |
| 5,001,139 | A | 3/1991 | Lawter et al. |
| 5,023,252 | A | 6/1991 | Hseih |
| 5,132,324 | A | 7/1992 | Meglasson |
| 5,384,308 | A | 1/1995 | Henkin |
| 5,525,329 | A | 6/1996 | Snyder et al. |
| 5,614,627 | A | 3/1997 | Takase et al. |
| 5,707,802 | A | 1/1998 | Sandhu et al. |
| 5,714,993 | A | 2/1998 | Keoshkerian et al. |
| 5,788,967 | A | 8/1998 | Henkin |
| 5,849,741 | A | 12/1998 | Watanabe et al. |
| 5,859,006 | A | 1/1999 | Daugan |
| 5,869,516 | A | 2/1999 | Arlt et al. |
| 6,207,703 | B1 | 3/2001 | Ponikau |
| 6,387,639 | B1 | 5/2002 | Posner et al. |
| 6,929,925 | B1 | 8/2005 | Zuker et al. |
| 2006/0275801 | A1 | 12/2006 | Henkin |
| 2008/0318913 | A1* | 12/2008 | Fox et al. ...................... 514/171 |
| 2010/0227875 | A1 | 9/2010 | Henkin |

FOREIGN PATENT DOCUMENTS

| | | |
|---|---|---|
| WO | WO 96/26940 A1 | 9/1996 |
| WO | WO 96/41194 A1 | 12/1996 |
| WO | WO 97/03675 A1 | 2/1997 |
| WO | WO 97/03985 A1 | 2/1997 |
| WO | WO 97/43287 A1 | 11/1997 |
| WO | WO 98/17668 A1 | 4/1998 |
| WO | WO 98/49166 A1 | 11/1998 |
| WO | WO 99/21562 A1 | 5/1999 |
| WO | WO 99/30697 A2 | 6/1999 |
| WO | WO 01/48477 A1 | 7/2001 |
| WO | WO 03/025224 A2 | 3/2003 |
| WO | WO 03/025224 A3 | 11/2003 |
| WO | WO 2008141438 A1 * | 11/2008 |

OTHER PUBLICATIONS

Ajani, et al. Alcohol consumption and risk of coronary heart disease by diabetes status. Circulation. Aug. 1, 2000;102(5):500-5.
Atkinson, et al. The pathogenesis of insulin-dependent diabetes mellitus. New Engl. J. Med. 1994;331:1428-1436.
Bakalyar, et al. Identification of a specialized adenylyl cyclase that may mediate odorant detection. Science. Dec. 7, 1990;250(4986):1403-6.
Bogardus, et al. Relationships between insulin secretion, insulin action, and fasting plasma glucose concentration in nondiabetic and noninsulin-dependent diabetic subjects. J Clin Invest. Oct. 1984;74(4):1238-46.
Borisy, et al. High-affinity cAMP phosphodiesterase and adenosine localized in sensory organs. Brain Res. May 7, 1993;610(2):199-207.
Breer. Molecular reaction cascades in olfactory signal transduction. J Steroid Biochem Mol Biol. Oct. 1991;39(4B):621-5.
Carlsson, et al. Alcohol consumption and the increase of Type II diabetes: Finnish twin cohort study. Diabetes Care. 2003, 26: 2785-2790.
Chou. Wake up and smell the coffee. Caffeine, coffee, and the medical consequences. West J Med. Nov. 1992;157(5):544-53.
Doty, et al. Human odor intensity perception: correlation with frog epithelial adenylate cyclase activity and transepithelial voltage response. Brain Res. Sep. 10, 1990;527(1):130-4.
Franz, et al. Evidence-based nutrition principles and recommendations for diabetes and related complications. Diabetes Care. 2002, 25:148-198.
Henkin, et al. Aberrant signaling in the olfactory system: a mechanism for smell loss. FASEB Journal, vol. 18, No. 4-5, pp. Abst. 792.7, 2004.
Henkin, et al. Insulin receptors as well as insulin are present in saliva and nasal mucus. Journal of Investigative Medicine. 2006; 54(Suppl. 2):S378.
Henkin, et al. Nasal seroproteins: a new frontier in the exploration of physiology and pathology of nasal and sinus disease. New Frontiers in Immunobiology. 2000; pp. 127-152.
Henkin, et al. Treatment of abnormal chemsensation in human taste and smell. In: Norris DM, ed. Perception of Behavioral Chemicals. Amsterdam, netherlands: Elsevier/North Holland Biomedical Press; 1981:227-265.
Henkin. Olfaction in human disease. In: English GM, ed. Loose-leaf Series of Otolaryngology. New York, NY: Harper and Row; 1982:1-39.

(Continued)

*Primary Examiner* — Samira Jean-Louis
(74) *Attorney, Agent, or Firm* — Wilson Sonsini Goodrich & Rosati, P.C.

(57) ABSTRACT

Methods and compositions are disclosed for the treatment of diseases or conditions produced by or associated with low cyclic nucleotide levels. The compositions comprise phosphodiesterase inhibitors and are formulated for intranasal and pulmonary administration.

17 Claims, 5 Drawing Sheets

(56) References Cited

OTHER PUBLICATIONS

Huque, et al. Odorant- and guanine nucleotide-stimulated phosphoinositide turnover in olfactory cilia. Biochem Biophys Res Commun. May 29, 1986;137(1):36-42.
Kurihara, et al. High activity of adenyl cyclase in olfactory and gustatory organs. Biochem Biophys Res Commun. Jul. 11, 1972;48(1):30-4.
Lancet, et al. Molecular transduction in smell and taste. Cold Spring Harb Symp Quant Biol. 1988;53 Pt 1:343-8.
Law, et al. Distribution of calmodulin in taste buds. Life Sci. 1985; 36:1189-1195.
Law, et al. Low parotid saliva calmodulin in patients with taste and smell dysfunction. Biochem Med Metab Biol. Aug. 1986;36(1):118-24.
Law, et al. Zinc deficiency decreases the activity of calmodulin regulated cyclic nucleotide phosphodiesterases in vivo in selected rat tissues. Biol Trace Elem Res. Aug. 1988;116(3):221-6.
Lowe, et al. Contribution of the ciliary cyclic nucleotide-gated conductance to olfactory transduction in the salamander. J Physiol. Mar. 1993;462:175-96.
Maitra, et al. The pancreas in Pathological Basis of Disease. 7th Edition. Elsevier. 2004; pp. 1155-1207.
Margolskee. The biochemistry and molecular biology of taste transduction. Curr Opin Neurobiol. Aug. 1993;3(4):526-31.
McAuley, et al. Diagnosing insulin resistance in the general population. Diabetes Care. Mar. 2001;24(3):460-4.
Nakajima, et al. Studies on cyclic nucleotides in brochopulmonary diseases with special reference to cAMP, cGMP in patients with nasal allergy and bronchial asthma. Acta Med. Kinki Univ., 4, 257-272, 1979.
Nakamura, et al. Proceedings of the 25th Japanese Symposium on Taste and Smell: 1. Current and Ca influx induced by intracellular cAMP in the newt olfactory receptor. Chem Sense. 1991; 17:85-116.
Pelangaris, et al. Oncogenic co-operation in beta-cell tumorigenesis. Endocr Relat Cancer. Dec. 2001;8(4):307-14.
Philips, et al. Factors determining the appearance of glucose in upper and lower respiratory tract secretions. Intensive Care Med. Dec. 2003;29(12):2204-10.
Riste, et al. High prevalence of Type 2 diabetes in all ethnic groups, including Europeans, in a British Inner City. Diabetes Care. 2001;24:1377-1383.
Schiffman, et al. Methyl xanthines enhance taste: evidence for modulation of taste by adenosine receptor. Pharmacol Biochem Behav. Feb. 1985;22(2):195-203.
Shirley, et al. Olfactory adenylate cyclase of the rat. Stimulation by odorants and inhibition by Ca2+. Biochem J. Dec. 1, 1986;240(2):605-7.
Sklar, et al. The odorant-sensitive adenylate cyclase of olfactory receptor cells. Differential stimulation by distinct classes of odorants. J Biol Chem. Nov. 25, 1986;261(33):15538-43.
Sobottka, et al. Disseminated *Encephalitozoon* (Septata) *intestinalis* infection in a patient with AIDS: novel diagnostic approaches and autopsy-confirmed parasitological cure following treatment with albendazole. J Clin Microbiol. Nov. 1995;33(11):2948-52.
Suzuki. Proceedings of the 21st Japanese Symposium on Taste and Smell: cyclic nucleotides as intracellular messengers in the olfactory transduction process. Chem Sense. 1988; 13:311-332.
The Expert Committee. Report of the Expert Committee on the Diagnosis and Classification of Diabetes Mellitus. Diabetes Care. 2003;26:S5-S20.
Vaughan. Second wind for second-messenger research. Bioscience. 1987; 37:642-646.
Velicu, et al. Insulin is present in human saliva and nasal mucus. Journal of Investinagtive Medicine. 2006; 54:S385.
Weinstock, et al. Olfactory dysfunction in humans with deficient guanine nucleotide-binding protein. Nature. Aug. 14-20, 1986;322(6080):635-6.
Weyer, et al. The natural history of insulin secretory dysfunction and insulin resistance in the pathogenesis of type 2 diabetes mellitus. J Clin Invest. Sep. 1999;104(6):787-94.
Will, et al. Cigarette smoking and diabetes mellitus from a large prospective cohort study. Int. J. Epidemiol. 2001; 30: 540-546.
Williams, G. Diabetes. In Endocrine Disorder. Oxford Testbook of Medicine. vol. 2, 4th Edition, Oxford Univ. Press 2003, pp. 317-359.
Woods, et al. Effect of hyperglycaemia on glucose concentration of human nasal secretions. Clin Sci (Lond). May 2004;106(5):527-33.
U.S. Appl. No. 13/421,277, filed Mar. 15, 2012, Henkin.
Abbott Axsym system. Theophylline II package insert. Abbott Laboratories. 2003.
FDA. Guidance for industry. Estimating the maximum safe starting dose in initial clinical trials for therapeutics in adult healthy volunteers. Center for Drug Evaluation and Research. Jul. 2005.
Anholt, et al. Molecular neurobiology of olfaction. Crit. Rev. Neurobiol. 1993;7:1-22.
Asakura, et al. cAMP and cGMP in the human parotid saliva. Arch. Otorhinolaryngol. 1980;226:145-154.
Bromley, et al. Smell and taste disorders: a primary care approach. Amer. Fam. Physician. 2000;61:427-436.
Cai, et al. Neuronal cyclic AMP controls the developmental loss in ability of axons to regenerate. J. Neurosci. 2001;21:4731-4739.
Cai, et al. Prior exposure to neurotrophins blocks inhibition of axonal regeneration by MAG and myelin via a cAMP dependent mechanism. Neuron. 1999;22:89-101.
Church, et al. Hyposmia associated with atopy. Ann. Aller. 1978;40:105-109.
Cullen, et al. Disorders of smell and taste. Med. Clin. North Amer. 1999;83:57-74.
Davidson, et al. Smell impairment: can it be reversed? Postgrad. Med. 1995;98:107-109, 112-118.
Deems, et al. Smell and taste disorders, a study of 750 patients from the University of Pennsylvania Smell and Taste Center. Arch. Otolaryngol. Head Neck Surg. 1991;177:519-528.
Doerty, et al. Carbonic anhydrase (CA) activity in nasal mucus appears to be a marker for loss of smell (hyposmia) in humans. J. Invest. Med. 1997;45:237A.
Firestein, et al. Regulation of sensory neuron precursor proliferation by cyclic GMP-dependent protein kinase. J. Neurochem. 1998;71:1846-1853.
Firestein, et al. Single odor-sensitive channels in olfactory receptor neurons are also gated by cyclic nucleotides. J. Neurosci. 1991;11:3565-72.
Glenert, et al. A single assay for cyclic adenosine 3':5'-monophosphate in human saliva. J. Cyclic Nucleotide Protein Phosphor. Res. 1985;10:451-461.
Harris, et al. Clinical evaluation and symptoms of chemosensory impairment: one thousand consecutive cases from the Nasal Dysfunction Clinic in San Diego. Amer. J. Rhinol 2006;20:101-108.
Henkin, et al. A double blind study of the effects of zinc sulfate on taste and smell dysfunction. Amer. J. Med. Sci. 1976;272: 285-299.
Henkin, et al. A zinc protein isolated from human parotid saliva. Proc. Nat. Acad. Sci. USA 1975;72:488-492.
Henkin, et al. Age related changes in cyclic nucleotides in saliva and nasal mucus possible feedback mechanism in development of gustatory and olfactory receptor function. FASEB J. 2005;19:A1368.
Henkin, et al. cAMP and cGMP in human parotid saliva: relationships to taste and smell dysfunction, gender and age. Amer. J. Med. Sci. 2007;334:431-440.
Henkin, et al. cAMP and cGMP in nasal mucus related to severity of smell loss in patients with smell dysfunction. Clinical Invest. Med. 2008;31:E78-E84.
Henkin, et al. cAMP and cGMP in nasal mucus: relationships to taste and smell dysfunction, gender and age. Clinical Invest. Med. 2008;31:E71-E77.
Henkin, et al. Decreased parotid saliva gustin/carbonic anhydrase VI secretion: an enzyme disorder manifested by gustatory and olfactory dysfunction. Amer. J. Med. Sci. 1999;318:380-391.
Henkin, et al. Decreased parotid salivary cyclic nucleotides related to smell loss severity in patients with taste and smell dysfunction. Metabolism. Dec. 2009;58(12):1717-23. doi: 10.1016/j.metabol. 2009.05.027. Epub Jul. 23, 2009.

(56) References Cited

OTHER PUBLICATIONS

Henkin, et al. Effective treatment of smell loss with theophylline. Exper. Biol. 2008;22:B976.2.
Henkin, et al. Efficacy of exogenous zinc in treatment of patients with carbonic anhydrase VI deficiency. Amer. J. Med. Sci. 1999;318:392-404.
Henkin, et al. Fractionation of human parotid saliva. J. Biol. Chem. 1978;253:7556-7565.
Henkin, et al. Hypogeusia, dysgeusia, hyposmia and dysosmia following influenza-like infection. Ann. Otol. Rhin. Laryngol. 1975;84:672-682.
Henkin, et al. Idiopathic hypogeusia with dysgeusia, hyposmia and dysosmia: a new syndrome. J. Amer. Med. Assoc. 1971;217:434-440.
Henkin, et al. Intranasal theophylline treatment of hyposmia and hypogeusia. Arch Otolaryngol Head/Neck Surg. 2012; 138(11):1-7.
Henkin, et al. Nasal seroproteins: a new frontier in the exploration of physiology and pathology of nasal and sinus disease. New Frontiers in Immunobiology in Otolaryngology (Veldman, J.E., Passali, D., Lim, D.J., Eds.), Kugler, The Hague, 2000, pp. 127-152.
Henkin. Dichotomous changes in cAMP and cGMP in human parotid saliva after oral theophylline. FASEB J. 2003;17:A1028.
Henkin. Effects of ACTH, adrenocorticosteroids and thyroid hormone on sensory function, in Anatomical Neuroendocrinology, (Stumpf, W.E., Grant, L.D., Eds.), Karger, A.G., Basel, 1975, pp. 298-316.
Henkin. Evaluation and treatment of human olfactory dysfunction, in Otolaryngology (English, G.M. Ed.), Lippincott, Philadelphia, 1993, vol. 2, pp. 1-86.
Henkin. Taste and smell disorders, human. Encyclopedia of Neuroscience, 3rd Ed., (Adelman, G., Smith, B.H., Eds.), Birkhauser, Boston, 2004.
Henkin. The definition of primary and accessory areas of olfaction as the basis for a classification of decreased olfactory acuity, in Olfaction and Taste II, (Hayashi, T. Ed.), Pergamon Press, London, 1967, pp. 235-252.
Henkin. The role of adrenal corticosteroids in sensory processes, in Adrenal Gland, (Blaschko, H., Sayers, G., Smith, A.D., Eds.), Handbook of Physiology. Endocrinology, Washington, DC. Amer. Physiol. Soc., Sect. 7, vol. VI, 1975, pp. 209-230.
Henkin. Zinc, saliva and taste: Interrelationships of gustin, nerve growth factor, saliva and zinc, in Zinc and Copper in Clinical Medicine, (Hambidge, K.M., Nichols, B.L., Eds.), Spectrum Publ. Inc., Jamaica, NY, 1978, pp. 35-48.
Kanamori, et al. Origin of cyclic adenosine monophosphate in saliva. J. Dent. Res. 1975;54:535-539.
Levy, et al. Increased brain activation in response to odors in patients with hyposmia after theophylline treatment demonstrated by fMRI. J. Comp. Asst. Tomog. 1998;22:760-770.
Moon, et al. Regulation of intracellular cyclic GMP levels in olfactory sensory neurons. J. Neurochem. 2005;95:200-9.
Neumann, et al. Regeneration of sensory axons within the injured spinal cord induced by intraganglionic cAMP elevation. Neuron. 2002;34:885-893.
Pace, et al. Odorant-sensitive adenylate cyclase may mediate olfactory reception. Nature. 1985;316:255-8.
Papathanassiu, et al. cAMP is present in human nasal mucus and may act as a growth factor in cells of the olfactory epithelium. FASEB J. 2002;16:A1153.
Rosezweig, et al. Possible novel mechanism for bitter taste mediated through cGMP. J. Neurophysiol. 1999;81: 1661-5.
Schaeffer, et al. Detection of cAMP in parotid saliva of normal individuals. J. Dent. Res. 1973;52:629.
Schechter, et al. Abnormalities of taste and smell following head trauma. J. Neurol. Neurosurg. Psychiat. 1974;37:802-810.
Schechter, et al. Idiopathic hypogeusia: a description of the syndrome and a single blind study with zinc sulfate, in Internat. Rev. Neurobiol. Suppl. 1., (Pfeiffer, C., Ed.), Academic Press, NY, 1972, pp. 125-133.
Seiden, et al. Office management of taste and smell disorders. Otolaryngol. Clin. North Amer. 1992;25:817-835.
Shepherd, et al. Sensory transduction entering the mainstream of membrane signaling. Cell. 1991;67:845-851.
Temmel, et al. Characteristics of olfactory disorders in relation to major causes of olfactory loss. Arch. Otolaryngol. Head Neck Surg. 2002;128:635-641.
Thompson. Cyclic nucleotide phosphodiesterase: pharmacology, biochemistry and function. Pharmacol. Ther. 1991;51:13-33.
Velicu, et al. On the antiapoptotic mechanism of action of theophylline in restoring smell function in patients with hyposmia. J. Invest. Med. 2005;53(Suppl. 2):5402.
Wysocki, et al. National Geographic Smell Survey: Effects of age are heterogeneous. Ann. NY Acad. Sci. 1989;561:12-28.
Lee, et al. Thiolated chitosan nanoparticles enhance anti-inflammatory effects of intranasally delivered theophylline. Respir Res. Aug. 24, 2006;7:112.

\* cited by examiner

PHOSPHODIESTERASE INHIBITOR TREATMENT

CROSS-REFERENCE

This application claims the benefit of U.S. Provisional Application No. 61/083,147, filed Jul. 23, 2008, incorporated herein by reference in its entirety.

BACKGROUND OF THE INVENTION

Phosphodiesterases (PDE) are a diverse family of enzymes that hydrolyse cyclic nucleotides resulting in the modulation of intracellular levels of the second messangers cAMP and cGMP, and hence, cell function. Numerous diseases and conditions result from low levels of cyclic nucleotides. The use of PDE inhibitors to raise cellular levels of cyclic nucleotides offers the ability to prevent, treat, or ameliorate diseases, conditions or their symptoms, however, systemic administration may not achieve therapeutically effective concentrations due to unacceptable side effects or to inability to obtain therapeutic levels in clinically responsive tissues. There is a need for suitable compositions and methods of delivery to achieve medically relevant concentrations of PDE inhibitors without unacceptable side effects. The present invention addresses these unmet needs.

SUMMARY OF INVENTION

In one aspect of the invention, a method is provided for treating anosmia, hyposmia, ageusia, or hypogeusia comprising administering by intranasal administration to a patient, an effective amount of a phosphodiesterase (PDE) inhibitor that treats the patient's anosmia, hyposmia, ageusia, or hypogeusia. In one embodiment, the PDE inhibitor is a non-selective PDE inhibitor, PDE-1 selective inhibitor, PDE-2 selective inhibitor, PDE-3 selective inhibitor, PDE-4 selective inhibitor, or a PDE-5 selective inhibitor. In another embodiment, the non-selective PDE inhibitor is a methylxanthine derivative. In a further embodiment the methylxanthine derivative is caffeine, theophylline, IBMX (3-isobutyl-1-methylxanthine) aminophylline, doxophylline, cipamphylline, neuphylline, pentoxiphylline, or diprophylline. In a particular embodiment, the methylxanthine derivative is theophylline or pentoxiphylline. In one embodiment the PDE-3 inhibitor is cilostazol.

In some embodiments, the effective amount of the PDE inhibitor is less than 2 mg. In other embodiments, the effective amount is less than 1 mg, 500 µg, 250µ, or 100 µg. In one embodiment, the effective amount is 40 µg.

In some embodiments, the PDE inhibitor is formulated as a liquid, while in other embodiments it is formulated as a dry powder. In some embodiments, the PDE inhibitor is administered as a liquid, gel, ointment, cream, spray, aerosol, or dry powder. In other embodiments, the PDE inhibitor is administered at least once, twice, or thrice daily.

In some embodiments, successful treatment of anosmia or hyposmia increases a patient's taste or smell acuity by at least 5%. In other embodiments, taste or smell acuity is measured objectively, while in other embodiments, acuity is measured subjectively. In some embodiments, the increase in taste or smell acuity is accompanied by an increase in nasal mucus or saliva cAMP or cGMP levels. In further embodiments, the increase in salivary or nasal mucus cAMP or cGMP level is at least 10% over the untreated level.

In one aspect of the invention, a method is provided for treating anosmia or hyposmia comprising administering to a patient in need, an effective amount of a PDE inhibitor, wherein the blood concentration of the PDE inhibitor does not exceed 1 mg/dl.

In another aspect of the invention, a method is provided for increasing nasal mucus or saliva cyclic adenosine 3',5'-monophosphate (cAMP) or cyclic guanosine 3',5'-monophosphate (cGMP) levels comprising administering by intranasal administration to a patient in need, an effective amount of a phosphodiesterase (PDE) inhibitor, whereby the cAMP or cGMP levels are increased at least 10% over the untreated level.

In one aspect, a method is provided for increasing taste or smell acuity comprising administering to a patient in need, an effective amount of a PDE inhibitor, wherein the PDE inhibitor is administered by intranasal administration and wherein taste or smell acuity is increased. In some embodiments, taste or smell acuity is increased at least 5% or 10% over pretreatment levels. In some embodiments, taste or smell acuity is measured objectively, while in other embodiments, it is subjectively. In further embodiments, the increase in taste or smell acuity is accompanied by an increase in nasal mucus or saliva cAMP or cGMP levels. In some embodiments, nasal mucus or saliva cAMP or cGMP levels increase at least 10% compared to the untreated state.

In another aspect, a method is provided for compensating for a pathologic rate of cAMP or cGMP metabolism comprising administering to a patient in need, an effective amount of a PDE inhibitor, wherein the PDE inhibitor is administered by intranasal administration and wherein cAMP or cGMP metabolism is decreased. In some embodiments, the blood concentration of the PDE inhibitor does not exceed 1 mg/dl.

In one aspect of the invention, a method is provided for screening patients for suitability for PDE inhibitor therapy for anosmia, hyposmia, ageusia or hypogeusia by administering to a patient a challenge dose of a PDE inhibitor; determining the nasal mucus or salivary level of cGMP; and comparing the patient's cGMP level to a threshold value, wherein patients who have a cGMP level equal to or greater than the threshold value are candidates for PDE inhibitor therapy to treat anosmia, hyposmia, ageusia or hypogeusia.

In another aspect of the invention, a pharmaceutical composition for intranasal administration is provided comprising a phosphodiesterase (PDE) inhibitor, wherein the composition comprises less than 1 mg of the PDE inhibitor and a pharmaceutically acceptable carrier. In some embodiments, the PDE inhibitor is selected from the group consisting of non-selective PDE inhibitors, PDE-1 selective inhibitors, PDE-2 selective inhibitors, PDE-3 selective inhibitors, PDE-4 selective inhibitors, and PDE-5 selective inhibitors. In some embodiments, the PDE inhibitor is a non-selective PDE inhibitor, while in other embodiments, the non-selective PDE inhibitor is a methylxanthine derivative. In further embodiments, the methylxanthine derivative is caffeine, theophylline, IBMX (3-isobutyl-1-methylxanthine) aminophylline, doxophylline, cipamphylline, neuphylline, pentoxiphylline, or diprophylline. In one embodiment, the methylxanthine derivative is theophylline or pentoxiphylline. In a further embodiment, the PDE inhibitor is a PDE-3 selective inhibitor. In a still further embodiment, the PDE-3 selective inhibitor is cilostazol.

In some embodiments the composition is a dry powder. In other embodiments, the dry powder composition further comprises an excipient. In further embodiments, the composition is a liquid. In some embodiments, the liquid composition further comprises an excipient. In further embodiments, the excipient is a preservative.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
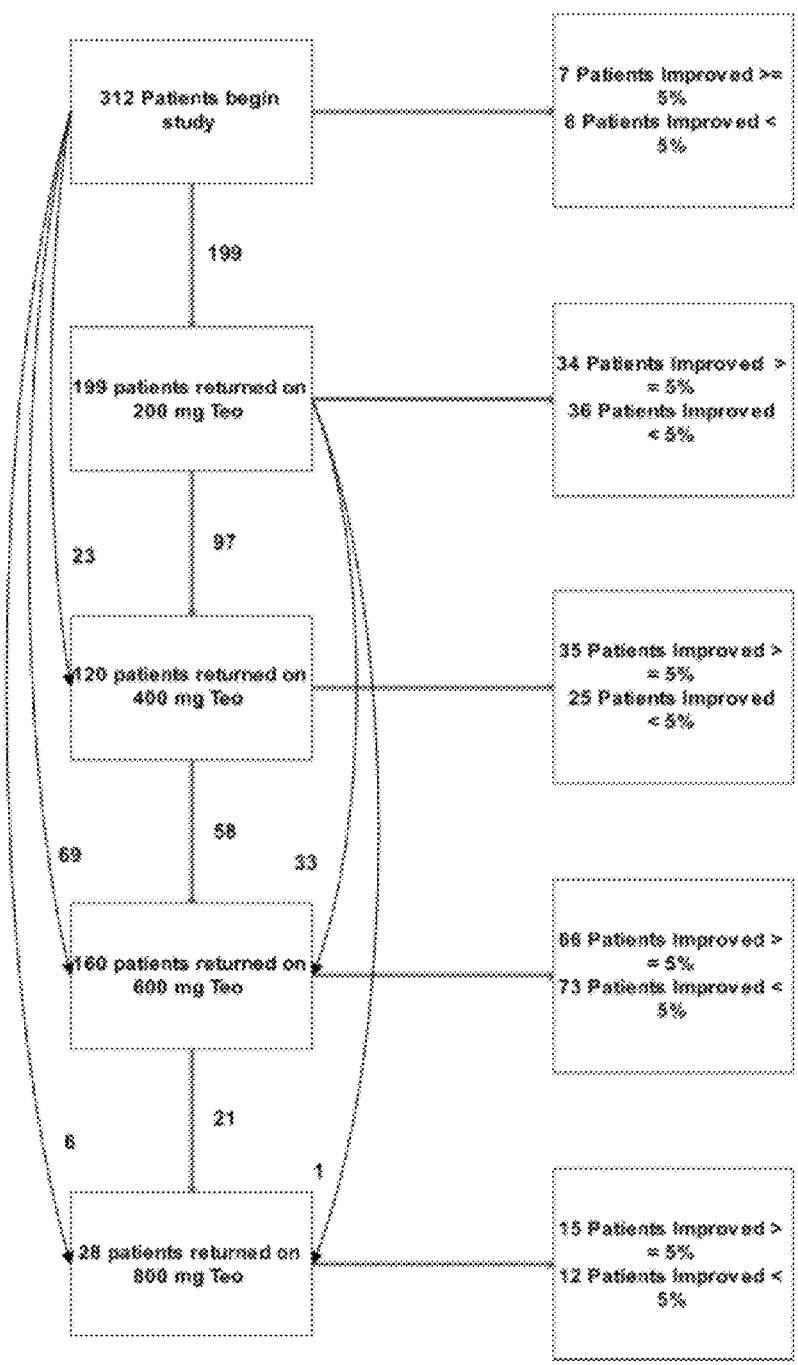
FIG. 1 illustrates the structure of the patient flow of the clinical trial showing the number and percentage of patients that returned on theophylline treatment. Three hundred twelve patients began the study on 200 mg. If improved <5% patient number indicates progression to next step up in dose (400 mg, 600 mg, 800 mg). Left sided numbers (lines) indicate numbers of distant patients who returned for first time (see text). Right sided numbers (lines) indicate patient numbers who improved <5% and returned on a higher dose. Difference between right sided numbers and patient numbers who improved <5% (in right boxes) indicate number of patient drop outs at each dose. If improved ≥5% patient data not included in further step-up doses.

Numerous PDEs are known with notable PDEs, their inhibitors and uses for these inhibitors listed below.

Theophylline and papaverine are representative members of non-specific PDE inhibitors that are prescribed orally to treat asthma and chronic obstructive pulmonary disease (COPD) through the relaxation of smooth muscle in the airways. Theophylline has anti-inflammatory effects on the airways that is useful to combat the abnormal inflammation seen in asthmatics. Most importantly, this anti-inflammatory effect is found at levels in the blood well below that which causes the common side effects seen in most people. Patients with emphysema and chronic bronchitis can also be helped with theophylline when their symptoms are partially related to reversible airway narrowing.

Theophylline is a methylxanthine derivative; other non-selective phosphodiesterase inhibitors in this class include caffeine, IBMX (3-isobutyl-1-methylxanthine, aminophylline, doxophylline, cipamphylline, theobromine, pentoxifylline (oxpentifylline) and diprophylline.

PDE1 selective inhibitors formerly known as calcium- and calmodulin-dependent phosphodiesterases include eburnamenine-14-carboxylic acid ethyl ester (vinpocetine), used to induce vasorelaxtion on cerebral smooth muscle tissue.

PDE2 decreases aldosterone secretion and is suggested to play an important role in the regulation of elevated intracellular concentrations of cAMP and cGMP in platelets. Several regions of the brain express PDE2 and rat experiments indicate that inhibition of PDE2 enhances memory. PDE2 may play a role in regulation of fluid and cell extravasation during inflammatory conditions as PDE2 is localized to microvessels, especially venous capillary and endothelial cells, but apparently not to larger vessels. PDE2 may also be a good pharmacological target for pathological states such as sepsis or in more localized inflammatory responses such as thrombin-induced edema formation in the lung. PDE-2 selective inhibitors include EHNA (erythro-9-(2-hydroxy-3-nonyl)adenine), 9-(6-phenyl-2-oxohex-3-yl)-2-(3,4-dimethoxybenzyl)-purin-6-one (PDP), and BAY 60-7750.

The PDE3 family hydrolyzes cAMP and cGMP, but in a manner suggesting that in vivo, the hydrolysis of cAMP is inhibited by cGMP. They also are distinguished by their ability to be activated by several phosphorylation pathways including the PKA and PI3K/PKB pathways. PDE3A is relatively highly expressed in platelets, as well as in cardiac myocytes and oocytes. PDE3B is a major PDE in adipose tissue, liver, and pancreas, as well as in several cardiovascular tissues. Both PDE3A and PDE3B are highly expressed in vascular smooth muscle cells and are likely to modulate contraction.

PDE3 inhibitors mimic sympathetic stimulation to increase cardiac inotropy, chronotropy and dromotropy. PDE3 inhibitors also antagonize platelet aggregation, increase myocardial contractility, and enhance vascular and airway smooth muscle relaxation. PDE3A is a regulator of this process and PDE3 inhibitors effectively prevent aggregation. In fact one drug, cilastazol (Pletal), is approved for treatment of intermittent claudication. Its mechanism of action is thought to involve inhibition of platelet aggregation along with inhibition of smooth muscle proliferation and vasodilation. PDE3-selective inhibitors include enoximone, milrinone (Primacor), amrinone, cilostamide, cilostazol (Pletal) and trequinsin.

PDE4 inhibitors can effectively suppress release of inflammatory mediators e.g., cytokines, inhibit the production of reactive oxygen species and immune cell infiltration. PDE4-selective inhibitors include mesembrine, rolipram, Ibudilast, a neuroprotective and bronchodilator drug used mainly in the treatment of asthma and stroke, and roflumilast (Daxas) and cilomilast (Airflo), currently in phase III clinical trials for treatment of chronic obstructive pulmonary disease. Other inflammatory diseases for which PDE4 inhibitors are currently being developed include asthma, arthritis, and psoriasis.

PDE5 is a regulator of vascular smooth muscle contraction best known as the molecular target for several well-advertised drugs used to treat erectile dysfunction and pulmonary hypertension. In the lung, inhibition of PDE5 opposes smooth muscle vasoconstriction, and PDE5 inhibitors are in clinical trials for treatment of pulmonary hypertension.

PDE5-selective inhibitors include Sildenafil, tadalafil, vardenafil, udenafil and avanafil.

PDE inhibitors inhibit cellular apoptosis by inhibiting TNF alpha, TRAIL and their metabolites. PDE inhibitors activate the production and secretion of nitric oxide in all tissues thereby inducing vasorelaxation or vasodilation of all blood vessels including those of the peripheral blood vessels (inhibiting intermittent claudication), the distal extremities and in the penile region contributing to penile erection.

PDE inhibitors useful in the present invention include, for example, filaminast, piclamilast, rolipram, Org 20241, MCI-154, roflumilast, toborinone, posicar, lixazinone, zaprinast, sildenafil, pyrazolopyrimidinones (such as those disclosed in WO 98/49166), motapizone, pimobendan, zardaverine, siguazodan, CI-930, EMD 53998, imazodan, saterinone, loprinone hydrochloride, 3-pyridinecarbonitrile derivatives, denbufyllene, albifylline, torbafylline, doxofylline, theophylline, pentoxofylline, nanterinone, cilostazol, cilostamide, MS 857, piroximone, milrinone, aminone, tolafentrine, dipyridamole, papaverine, E4021, thienopyrimidine derivatives (such as those disclosed in WO 98/17668), triflusal, ICOS-351, tetrahydropiperazino[1,2-b]beta-carboline-1,4-dione derivatives (such as those disclosed in U.S. Pat. No. 5,859,006, WO 97/03985 and WO 97/03675), carboline derivatives, (such as those disclosed in WO 97/43287), 2-pyrazolin-5-one derivatives (such as those disclosed in U.S. Pat. No. 5,869,516), fused pyridazine derivatives (such as those disclosed in U.S. Pat. No. 5,849,741), quinazoline derivatives (such as those disclosed in U.S. Pat. No. 5,614,627), anthranilic acid derivatives (such as those disclosed in U.S. Pat. No. 5,714,993), imidazoquinazoline derivatives (such as those disclosed in WO 96/26940), and the like. Also included are those phosphodiesterase inhibitors disclosed in WO 99/21562 and WO 99/30697. The disclosures of each of which are incorporated herein by reference in their entirety. In some embodiments, the intranasal composition does not comprise a PDE5 selective inhibitor.

Sources of information for the above, and other phosphodiesterase inhibitors include Goodman and Gilman, The Pharmacological Basis of Therapeutics (9th Ed.), McGraw-Hill, Inc. (1995), The Physician's Desk Reference (49th Ed.), Medical Economics (1995), Drug Facts and Comparisons (1993 Ed), Facts and Comparisons (1993), and The Merck Index (12th Ed.), Merck & Co., Inc. (1996), the disclosures of each of which are incorporated herein by reference in their entirety.

The following definitions are used throughout the specification.

"Phosphodiesterase inhibitor" or "PDE inhibitor" refers to any compound that inhibits a phosphodiesterase enzyme, isozyme or allozyme. The term refers to selective or non-selective inhibitors of cyclic guanosine 3',5'-monophosphate phosphodiesterases (cGMP-PDE) and cyclic adenosine 3',5'-monophosphate phosphodiesterases (cAMP-PDE).

"Patient" refers to animals, preferably mammals, more preferably humans.

Other medicaments may be combined with or administered contemporaneously with at least one PDE inhibitors to complement and/or to enhance the prevention or treatment effect of a PDE inhibitor. These other medicaments include vasoactive agents, anticholinergic agents, leukotriene receptor antagonists, thromboxane synthetase inhibitors, thromboxane $A_2$ receptor antagonist, mediator release inhibitor, antihistamic agent, cytokine inhibitor, prostaglandins, forskolin, elastase inhibitor, steroid, expectorant, or antibacterial agent. The other medicaments can be administered simultaneously with, subsequently to, or prior to administration of the PDE inhibitors.

In one embodiment, the patient is administered a therapeutically effective amount of a PDE inhibitor and a vasoactive agent. A vasoactive agent is any therapeutic agent capable of relaxing vascular smooth muscle. Suitable vasoactive agents include, but are not limited to, potassium channel activators (such as, for example, nicorandil, pinacidil, cromakalim, minoxidil, aprilkalim, loprazolam and the like); calcium blockers (such as, for example, nifedipine, veraparmil, diltiazem, gallopamil, niludipine, nimodipins, nicardipine, and the like); beta-blockers (such as, for example, butixamine, dichloroisoproterenol, propanolol, alprenolol, bunolol, nadolol, oxprenolol, perbutolol, pinodolol, sotalol, timolol, metoprolol, atenolol, acebutolol, bevantolol, pafenolol, tolamodol, and the like); long and short acting alpha-adrenergic receptor antagonist (such as, for example, phenoxybenzamide, dibenamine, doxazosin, terazosin, phentolamine, tolazoline, prozosin, trimazosin, yohimbine, moxisylyte and the like adenosine, ergot alkaloids (such as, for example, ergotamine, ergotamine analogs, including, for example, acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride); vasoactive intestinal peptides (such as, for example, peptide histidine isoleucine, peptide histidine methionine, substance P, calcitonin gene-related peptide, neurokinin A, bradykinin, neurokinin B, and the like); dopamine agonists (such as, for example, apomorphine, bromocriptine, testosterone, cocaine, strychnine, and the like); opioid antagonists (such as, for example, naltrexone, and the like); prostaglandins (such as, for example, alprostadil, prostaglandin $E_2$, prostaglandin $F_2$, misoprostol, enprostil, arbaprostil, unoprostone, trimoprostil, carboprost, limaprost, gemeprost, lantanoprost, omoprostil, beraprost, sulpostrone, rioprostil, and the like); endothelin antagonists (such as, for example, bosentan, sulfonamide endothelin antagonists, BQ-123, SQ 28608, and the like) and mixtures thereof.

In one aspect of the present invention, methods are provided to prevent or treat diseases associated with or caused by the increased (pathological) metabolism of cyclic adenosine 3',5'-monophosphate (cAMP) or cyclic guanosine 3',5'-monophosphate (cGMP), including, for example, anosmia, hyposmia, ageusia, hypogeusia, hypertension, pulmonary hypertension, congestive heart failure, renal failure, myocardial infraction, stable, unstable and variant (Prinzmetal) angina, atherosclerosis, cardiac edema, renal insufficiency, nephrotic edema, hepatic edema, stroke, asthma, bronchitis, chronic obstructive pulmonary disease (COPD), cystic fibrosis, dementia including Alzheimer's disease, immunodeficiency, premature labor, Parkinson's disease, multiple sclerosis, dysmenorrhoea, benign prostatic hyperplasis (BPH), bladder outlet obstruction, incontinence, conditions of reduced blood vessel patency, e.g., postpercutaneous transluminal coronary angioplasty (post-PTCA), peripheral vascular disease, allergic rhinitis, glaucoma, malignancies and diseases characterized by disorders of gut motility, e.g, irritable bowel syndrome (IBS), rheumatoid arthritis, systemic lupus erythematosus, psoriasis, and other autoimmune diseases, Huntington's chorea, and Amyotrophic lateral sclerosis (ALS), by administering to a patient in need thereof a therapeutically effective amount of the compounds and/or compositions described herein.

In some embodiments, the intranasal, pulmonary or lingual administration of a PDE inhibitor can increase cell, tissue or organ levels of cAMP or cGMP. In some embodiments, the increase in cAMP or cGMP levels is at least 10%, 20%, 30%, 40%, 50%, 60%, 70%, 80%, 90%, 100%, 200%, 300%, 400%, 500% or 1000% over the untreated state. In other embodiments, cAMP or cGMP levels are increased to at least 10%, 20%, 30%, 40%, 50%, 60%, 70%, 80%, 90%, 100%, 125%, 150%, 200%, 300%, 400%, or 500% of the levels seen in controls, i.e., normal individuals. In some embodiments of the invention, a method is provided for increasing nasal mucus or salivary cAMP or cGMP levels, wherein an effective amount of a PDE inhibitor is administered intranasally to a patient resulting in an increase in the cAMP or cGMP levels of at least 10%, 20%, 30%, 40%, 50%, 60%, 70%, 80%, 90%, 100%, 150%, 200%, 300%, 400%, 500%, or 1000% over the untreated level. In other embodiments, nasal mucus or salivary cAMP or cGMP levels are increased to at least 10%, 20%, 30%, 40%, 50%, 60%, 70%, 80%, 90%, 100%, 125%, 150%, 200%, 300%, 400%, or 500% of the levels seen in normal individuals.

In some embodiments, the administration of an effective amount of a PDE inhibitor by intranasal, lingual or pulmonary administration does not produce a detectable blood level of the PDE inhibitor. In some embodiments, the administration of an effective amount of a PDE inhibitor by intranasal, lingual or pulmonary administration produces blood concentration of the PDE inhibitor that are less than 5 mg/dl, 2 mg/dl, 1 mg/dl, 500 µg/dl, 250 µg/dl, 100 µg/dl, 50 µg/dl, 25 µg/dl, 10 µg/dl, 5 µg/dl, or 1 µg/dl.

In some embodiments, intranasal or lingual administration of an effective amount of a PDE inhibitor increases taste or smell acuity. In some embodiments, the increase in taste or smell acuity is at least 5%, 10%, 20%, 30%, 40%, 50%, 75%, or 100% compared to the untreated state. In other embodiments, taste or smell acuity is increased to at least 5%, 10%, 20%, 30%, 40%, 50%, 75%, or 100% of the acuity of normal individuals. In some embodiments, taste or smell acuity is measured objectively, while in other embodiments taste or smell acuity is measured subjectively.

When administered in vivo, the compounds and compositions of the present invention can be administered in combination with pharmaceutically acceptable carriers and in dosages described herein. The compounds and compositions of the present invention can be formulated as pharmaceutically acceptable neutral (free base) or salt forms. Pharmaceutically acceptable salts include, for example, those formed with free amino groups such as those derived from hydrochloric, hydrobromic, hydroiodide, phosphoric, sulfuric, acetic, citric, benzoic, fumaric, glutamic, lactic, malic, maleic, succinic, tartaric, p-toluenesulfonic, methanesulfonic acids, gluconic acid, and the like, and those formed with free carboxyl groups, such as those derived from sodium, potassium, ammonium, calcium, ferric hydroxides, isopropylamine, triethylamine, 2-ethylamino ethanol, histidine, procaine, and the like.

"Therapeutically effective amount" refers to the amount of a PDE inhibitor with or without additional agents that is effective to achieve its intended purpose. While individual patient needs may vary, determination of optimal ranges for effective amounts of each of the compounds and compositions is within the skill of an ordinary practitioner of the art. Generally, the dosage required to provide an effective amount of the composition, and which can be adjusted by one of ordinary skill in the art, will vary, depending on the age, health, physical condition, sex, weight, extent of the dysfunction of the recipient, frequency of treatment and the nature and scope of the dysfunction.

The amount of a given PDE inhibitor which will be effective in the prevention or treatment of a particular dysfunction or condition will depend on the nature of the dysfunction or condition, and can be determined by standard clinical techniques, including reference to Goodman and Gilman, supra; The Physician's Desk Reference, supra; Medical Economics Company, Inc., Oradell, N. J., 1995; and Drug Facts and Comparisons, Inc., St. Louis, Mo., 1993. The precise dose to be used in the formulation will also depend on the route of administration, and the seriousness of the dysfunction or disorder, and should be decided by the physician and the patient's circumstances.

The nasal and/or pulmonary administered PDE inhibitors can be used at dose ranges and over a course of dose regimen that are the same or substantially equivalent to those used for oral administration. The nasal and/or pulmonary administered PDE inhibitors can also be used in lower doses and in less extensive regimens of treatment. The amount of active ingredient that can be combined with one or more carrier material to produce a single dosage form will vary depending upon the host treated and the particular mode of administration.

Representative daily intranasal, lingual or pulmonary dosages are between about 1.0 µg and 2000 mg per day, between about 1.0 µg and 500.0 mg per day, between about 10 µg and 100.0 mg per day, between about 10 µg and about 10 mg per day, between about 10 µg and 1.0 mg per day, between about 10 µg and 500 µg per day or between about 1 µg and 50 µg per day of the active ingredient comprising a preferred compound. These ranges of dosage amounts represent total dosage amounts of the active ingredient per day for a given patient. In some embodiments, the daily administered dose is less than 2000 mg per day, 1000 mg per day, 500 mg per day, 100 mg per day, 10 mg per day, 1.0 mg per day, 500 µg per day, 300 µg per day, 200 µg per day, 100 µg per day or 50 µg per day. In other embodiments, the daily administered dose is at least 2000 mg per day, 1000 mg per day, 500 mg per day, 100 mg per day, 10 mg per day, 1.0 mg per day, 500 µg per day, 300 µg per day, 200 µg per day, 100 µg per day or 50 µg per day. In some embodiments, on a per kilo basis, suitable dosage levels of the compounds will be between about 0.001 µg/kg and about 10.0 mg/kg of body weight per day, between about 0.5 µg/kg and about 0.5 mg/kg of body weight per day, between about 1.0 µg/kg and about 100 µg/kg of body weight per day, and between about 2.0 µg/kg and about 50 µg/kg of body weight per day of the active ingredient. In other embodiments, the suitable dosage level on a per kilo basis is less than 10.0 mg/kg of body weight per day, 1 mg/kg of body weight per day, 500 µg/kg of body weight per day, 100 µg/kg of body weight per day, 10 µg/kg of body weight per day of the active ingredient, or 1.0 µg/kg of body weight per day of active ingredient. In further embodiments, the suitable dosage level on a per kilo basis is at least 10.0 mg/kg of body weight per day, 1 mg/kg of body weight per day, 500 µg/kg of body weight per day, 100 µg/kg of body weight per day, 10 µg/kg of body weight per day of the active ingredient, or 1.0 µg/kg of body weight per day of active ingredient.

In some embodiments, the individual or single intranasal, lingual and/or pulmonary dose of the PDE inhibitors is less than 10 mg, less than 2 mg, less than 1 mg, less than 500 µg, less than 200 µg, less than 100 µg, or less than 50 µg per dosage unit or application. In other embodiments, the individual or single intranasal, lingual and/or pulmonary dose of the PDE inhibitors is at least 10 mg, 1 mg, 500 µg, 200 µg, 100 µg, 50 µg per dosage unit or application. In further embodiments, the individual or single intranasal, lingual and/or pulmonary dose of the PDE inhibitors ranges from 1 µg to 10 mg, 10µ to 1 mg, 10 µg to 500 µg, 10 µg to 250 µg, 10 µg to 100 µg, 10 µg to 50 µg, 25 µg to 100 µg, 25 µg to 250 µg, 50 µg to 500 µg, or 100 µg to 1.0 mg The number of times per day that a dose is administered will depend upon such pharmacological and pharmacokinetic factors as the half-life of the active ingredient, which reflects its rate of catabolism and clearance, as well as the minimal and optimal blood plasma or other body fluid levels of said active ingredient attained in the patient which are required for therapeutic efficacy. Typically, the PDE inhibitors are given once, twice, trice, or four times daily. PDE inhibitors may also be administered on a less frequent basis, such as every other day, every three, four, five, six or seven days.

Other factors may also be considered in deciding upon the number of doses per day and the amount of active ingredient per dose to be administered. Not the least important of such other factors is the individual response of the patient being treated. Thus, for example, where the active ingredient is used to treat or prevent asthma, and is administered loco-regionally via aerosol inhalation into the lungs, from one to four doses consisting of actuations of a dispensing device, i.e., "puffs" of an inhaler, may be administered each day, with each dose containing from about 10.0 µg to about 10.0 mg of active ingredient.

Effective doses can be extrapolated from dose-response curves derived from in vitro or animal model test systems and are in the same ranges or less than as described for the commercially available compounds in the Physician's Desk Reference, supra.

Aerosols

By "aerosol" is meant any composition of a PDE inhibitor administered as an aerosolized formulation, including for example an inhalation spray, inhalation solution, inhalation suspension, a nebulized solution, or nasal spray. Aerosolized formulations can deliver high concentrations of a PDE inhibitor directly to the airways with low systemic absorption. Solutions for aerosolization typically contain at least one therapeutically active PDE inhibitor dissolved or suspended in an aqueous solution that may further include one or more excipients (e.g., preservatives, viscosity modifiers, emulsifiers, or buffering agents). The solution acts as a carrier for the PDE inhibitor. In some embodiments, the preservative is methylparaben or propylparaben. These formulations are intended for delivery to the respiratory airways by inspiration.

A major limitation of pulmonary delivery is the difficulty of reaching the deep lung. To achieve high concentrations of a PDE inhibitor solution in both the upper and lower respiratory airways, the PDE inhibitor solution is preferably nebulized in jet nebulizers, a ultrasonic nebulizer, or an electronic nebulizer particularly those modified with the addition of one-way flow valves, such as for example, the Pari LC Plus™ nebulizer, commercially available from Pari Respiratory Equipment, Inc., Richmond, Va., which delivers up to 20% more drug than other unmodified nebulizers.

The pH of the formulation is also important for aerosol delivery. When the aerosol is acidic or basic, it can cause bronchospasm and cough. The safe range of pH is relative and depends on a patient's tolerance. Some patients tolerate a mildly acidic aerosol, which in others will cause bronchospasm. Typically, an aerosol solution having a pH less than 4.5 induces bronchospasm. An aerosol solution having pH between 4.5 and 5.5 will occasionally cause this problem. The aerosol solution having a pH between 5.5 and 7.0 is usually considered safe. Any aerosol having pH greater than 7.0 is to be avoided as the body tissues are unable to buffer alkaline aerosols and result in irritation and bronchospasm. Therefore, the pH of the formulation is preferably maintained between 4.5 and 7.0, more preferably between 5.0 and 7.0 and most preferably between 5.5 and 6.5 to permit generation of a PDE inhibitor aerosol that is well tolerated by patients without any secondary undesirable side effects such as bronchospasm and cough. The osmolarity of the formulation can also be adjusted to osmolarities of about 250 to 350 mosm/L, according to the patient's tolerance.

Drops and Gels

In some embodiments, the PDE inhibitor is directly applied to the nasal or lingual epithelium as a liquid, cream, lotion, ointment or gel. These fluids or semifluids contain at least one therapeutically active PDE inhibitor and may further include at least one excipient (e.g., preservatives, viscosity modifiers, emulsifiers, or buffering agents) that are formulated for administration as nose drops, or applied with an applicator to the inside of the nasal passages. In some embodiments, the preservative is methylparaben or propylparaben. The pH of the formulation is preferably maintained between 4.5 and 7.0, more preferably between 5.0 and 7.0 and most preferably between 5.5 and 6.5. The osmolarity of the formulation can also be adjusted to osmolarities of about 250 to 350 mosm/L.

Dry Powder Formulation

As an alternative therapy to aerosol, liquid or gel delivery, the PDE inhibitor may be administered in a dry powder formulation for efficacious delivery into the nasal cavity and/or endobronchial space. Dry powder formulation is convenient because it does not require further handling by a physician, pharmacist or patient such as diluting or reconstituting the agent as is often required with nebulizers. Furthermore, dry powder delivery devices are sufficiently small and fully portable. Dry powder formulations may also be applied directly on the lingual epithelium.

For dry powder formulations, a PDE inhibitor and/or carrier is processed to median diameter ranging from 0.001-250 µm typically by media milling, jet milling, spray drying, super-critical fluid energy, or particle precipitation techniques. Particles of a desired size ranges can also be obtained through the use of sieves. Frequently, milled particles are passed through one or more sieves to isolate a desired size range. In some embodiments intended for pulmonary administration, the PDE inhibitor and/or carrier has a median diameter ranging from 0.01-25 µm, 0.1-10 µm, 1-10 µm, 1-5 µm, or 2-5 µm. In further embodiments intended for pulmonary administration, the PDE inhibitor and/or carrier has a median diameter ranging less than 20 µm, 10 µm, 5 µm, 4, µm, 3 µm, 2 µm, or 1 µm. In some embodiments intended for nasal administration, the PDE inhibitor and/or carrier has a median diameter ranging from 1-250 µm, 5-200 µm, 10-150 µm, 10-100 µm, 10-50 µm, 15-100 µm, 15-50 µm, or 20-60 µm. In further embodiments intended for nasal administration, the PDE inhibitor and/or carrier has a median diameter of less than 250 µm, 200 µm, 150 µm, 100 µm, 75 µm, 60 µm, 50 µm, 40 µm or 30 µm. In other embodiments intended for nasal administration, the PDE inhibitor and/or carrier has a median diameter of at least 20 µm, 30 µm, 40 µm, 50 µm, 60 µm, 75 µm, 100 µm, 150 µm or 200 µm.

In some embodiments, a pharmaceutically acceptable carrier for the present compositions and formulations include but are not limited to amino acids, peptides, proteins, non-biological polymers, biological polymers, simple sugars, carbohydrates, gums, inorganic salts and metal compounds which may be present singularly or in combination. In some embodiments, the pharmaceutically acceptable carrier comprises native, derivatized, modified forms, or combinations thereof.

In some embodiments, useful proteins include, but are not limited to, gelatin or albumin. In some embodiments, useful sugars that can serve as pharmaceutically acceptable carriers include, but are not limited to fructose, galactose, glucose, lactitol, lactose, maltitol, maltose, mannitol, melezitose, myoinositol, palatinite, raffinose, stachyose, sucrose, trehalose, xylitol, hydrates thereof, and combinations of thereof.

In some embodiments, useful carbohydrates that can serve as pharmaceutically acceptable carriers include, but are not limited to starches such as corn starch, potato starch, amylose, amylopectin, pectin, hydroxypropyl starch, carboxymethyl starch, and cross-linked starch. In other embodiments, useful carbohydrates that can serve as pharmaceutically acceptable carriers include, but are not limited to cellulose, crystalline cellulose, microcrystalline cellulose, α-cellulose, methylcellulose, hydroxypropyl cellulose, carboxymethyl cellulose, ethyl cellulose, hydroxypropyl methyl cellulose, and cellulose acetate.

In some embodiments, the composition or formulation includes an excipient. Useful excipients include, but are not limited to, fluidizers, lubricants, adhesion agents, surfactants, acidifying agents, alkalizing agents, agents to adjust pH, antimicrobial preservatives, antioxidants, anti-static agents, buffering agents, chelating agents, humectants, gel-forming agents, or wetting agents. Excipients also include coloring agents, coating agents, sweetening, flavoring and perfuming and other masking agents. The compositions and formulations of this invention may include a therapeutic agent with an individual excipient or with multiple excipients in any suitable combination, with or without a carrier.

The dry powder formulations of the present invention may be used directly in metered dose or dry powder inhalers. With dry powder inhalers, the inspiratory flow of the patient accelerates the powder out of the device and into the nasal and/or oral cavity. Alternatively, dry powder inhalers may employ an air source, a gas source, or electrostatics, to deliver the therapeutic agent. The dry powder formulations are temperature stable and have a physiologically acceptable pH of 4.0-7.5, preferably 6.5 to 7.0.

Kits/Articles of Manufacture

For use of the therapeutic compositions described herein, kits and articles of manufacture are also described. In some embodiments, such kits include a carrier, package, or container that is compartmentalized to receive one or more blister packs, bottles, tubes, capsules, and the like. In certain embodiments, the pharmaceutical compositions are presented in a pack or dispenser device which contains one or more unit dosage forms containing a compound provided herein. In other embodiments, the pack contains metal or plastic foil, such as a blister pack. In some embodiments, the pack contains capsules, vials, or tubes. In other embodiments, the pack or dispenser device is accompanied by instructions for administration. In some embodiments, the dispenser is disposable or single use, while in other embodiments, the dispenser is reusable. In certain embodiments, the pharmaceutical formulations are preloaded into the device.

In still other embodiments, the pack or dispenser also accompanied with a notice as required by a governmental agency regulating the manufacture, use, or sale of pharmaceuticals. This notice states that the drug is approved by the agency for human or veterinary administration. Such notice, for example, is the labeling approved by the U.S. Food and Drug Administration for prescription drugs, or the approved product insert. Compositions containing a compound provided herein formulated in a compatible pharmaceutical carrier are also prepared, placed in an appropriate container, and labeled for treatment of an indicated condition.

The articles of manufacture provided herein may also contain an administration or dispensing device. Examples of administration devices include pulmonary inhalers and intranasal applicators. Pumps may be provided with the inhalers and intranasal devices, or the pumps may be built into the devices. Alternatively, a propellant may be included with or it may be stored within the devices.

Such kits optionally comprise an identifying description or label for the containers. In further embodiments, the label is on a container with letters, numbers or other characters forming the label and attached, molded or etched into the container itself, a label is associated with a container when it is present within a receptacle or carrier that also holds the container, e.g., as a package insert. In some embodiments, a label is used to indicate that the contents are to be used for a specific therapeutic application. In yet other embodiments, the label also indicates directions for use of the contents, such as in the methods described herein. In some embodiments, a set of instructions may also be included, generally in the form of a package insert. The informational material may contain instructions on how to dispense the pharmaceutical composition, including description of the type of patients who may be treated, the schedule (e.g., dose and frequency), and the like.

The invention also relates to a set (kit) consisting of separate packs of kits that are frequently assembled for shipping or for patient convenience, such as a weekly, biweekly or monthly supply of a medicament.

EXPERIMENTAL SECTION

Example 1

Patients with smell loss (hyposmia) reflect a clinically diverse group of patients (1-10). Whereas there is common agreement that many patients exhibit this clinical problem, there is no agreement with respect to their treatment. Indeed, most groups who evaluate these patients consider that there are few, if any, medically relevant treatments for them.

In an attempt to elucidate the biochemical pathology of hyposmia, total protein fractionation was performed on saliva (14, 15) and nasal mucus (16), since these fluids bathe both taste buds and olfactory epithelial tissues, respectively, and contain substances which are critical to maintain these sense organs (14-16). It was discovered that some patients with smell loss had diminished salivary (17) and nasal mucus (18) levels of the saliva and nasal mucus protein carbonic anhydrase (CA) VI, a putative stem cell growth factor; treatment of these patients with exogenous zinc increases both salivary and nasal mucus CA VI (19) leading to an increase in smell acuity (19). These CAVI deficient patients, however, represent only a fraction of the total patient group (1, 2).

Further investigation revealed many of the non-CAVI deficient patients exhibited lower than normal levels of both cAMP and cGMP in their saliva (31) and nasal mucus (32). When the cAMP and cGMP levels in the saliva and in the nasal mucus of these patients was compared against the severity of their smell loss, it was noted that as smell loss severity increased (worsened) levels of these cyclic nucleotides in saliva (34) and nasal mucus (35) decreased. Since these cyclic nucleotides act as growth factors for several neural tissues (36-38) including olfactory tissues (39-45), it was reasoned that lower than normal levels of cyclic nucleotides may play a role in generation of their hyposmia. To test this hypothesis, patients were treated with the PDE inhibitor theophylline in an effort to increase saliva and nasal mucus levels of these cyclic nucleotides. It was found that hyposmia was corrected in many of them as demonstrated by improvement of psychophysical measurements of hyposmia, (1, 2, 49), by increased brain activation to several olfactory stimuli through measurements of functional magnetic resonance imaging (FMRI) (48) and associated with changes in serum theophylline (44).

In order to confirm these initial studies, theophylline was given to 312 patients in a fixed design, controlled, open trial over a period of seven years. These patients exhibited salivary (32) and nasal mucus (33) levels of cAMP and cGMP below the normal mean. Studies were approved by an Institutional Review Board and all patients gave informed consent.

The patients ranged in age from 18 to 86 y (55±1 y, mean±SEM) and consisted of 178 women, aged 18-85 y (55±2 y) and 134 men, aged 23-86 y (54±3 y). Patients reported a history of smell loss extending from 2 months to 40 y (6.5+1.0 y). Etiology of smell loss varied; the major causes of hyposmia were post influenza-like hyposmia [97 patients, 31.1% of the total (50)] and allergic rhinitis [97 patients, 31.1% of the total (51)] followed by head injury [42 patients, 13.5% (52)] and several other causes, as previously described [76 patients, 24.4% (1, 2)]. Levels of CA VI in their saliva and nasal mucus were within normal levels.

Patients initially reported their sensory dysfunction as either loss of taste (i.e., flavor) and/or smell function. This subjective response was documented by objective psychophysical measurements of olfactory function administered to each patient by use of a forced-choice, three-stimuli, stepwise-staircase technique in a fixed, controlled design (1, 53). Efficacy of this technique and results of testing were previously documented in a double-blind clinical trial (53). Four odors were used; they were pyridine (dead-fish odor), nitrobenzene (bitter-almond odor), thiophene (petroleum-like odor) and amyl acetate (banana-oil odor). Detection thresholds (DT), recognition thresholds (RT) and magnitude estimation (ME) values for each odor were determined as previously described (1, 53). Thresholds were converted into bottle units (BU) as previously described (53) and results reported as M±SEM of correct responses for each odor in each treatment group; ME was reported in % and results calculated to obtain M±SEM for each treatment group for all correct responses using data for the four highest odor concentrations presented (from $10^{-2M}$—an absolute odor concentration).

In addition, each patient graded the hedonic (H) value of each odor presented for these same odor concentrations (from $10^{-2M}$—an absolute odor concentration using a $-100-0 \mp 100$ scale). If they considered the presented odor pleasant ("they wished to smell the odor again") they graded the odor as $+1 \mp 100$ with respect to pleasantness; if they considered the odor unpleasant ("they did not wish to smell the odor again") they graded the odor as $-1--100$ with respect to unpleasantness; if they did not consider the odor either pleasant or unpleasant they graded the odor as neutral or 0. Results were obtained by calculating the arithmetical sum of each correct recognition response for each odor with respect to its pleasantness, unpleasantness or neutrality. Arithmetic M±SEM were obtained for each treatment group for each odor presented.

Independently, patients were also required to grade their ability to smell daily on a scale from 0-100, with 0 reflecting no overall smell function over a 24 hour period, 100 reflecting normal overall smell function over this period and numbers between 0-100 reflecting their estimation of their overall ability to smell odors over this period.

Based upon values for the DT, RT and ME tests, patients were classified with respect to severity of smell loss into the four types [(1, 2) (Table I)]. Anosmia is the complete loss of smell. Patients with anosmia have DT, RT and ME test values of zero, since they cannot detect, recognize nor grade the intensity of any odor including an absolute concentration of any odorant (Table I). No patients with anosmia were present in the study due to the relative rarity of this condition (1). Patients with Type I hyposmia (96 patients) could detect some odors but could not recognize any odor correctly; thus, DTs for some odors were present, but RTs and MEs for all odors were zero since they could neither recognize correctly nor thereby grade correctly intensity of any odor (Table I). Patients with Type II hyposmia (208 patients) could detect and recognize some odors, but at levels greater than normal; thus DTs and RTs were present, but elevated above normal and MEs were present but at levels lower than normal (Table I). Patients with Type III hyposmia (8 patients) could detect and recognize all odors at normal levels (i.e., normal DT and RT), but ME values for one or more odors were significantly decreased below normal (Table I). Severity of smell loss graded from most to least severe loss was typed as anosmia>hyposmia Type I>Type II>Type III and verified by demonstrating that as smell loss severity increased levels of nasal mucus cAMP and cGMP decreased (32, 34).

TABLE I

CLASSIFICATION OF SMELL LOSS

| | DETECTION THRESHOLD DT in M/L | RECOGNITION THRESHOLD RT in M/L | MAGNITUDE ESTIMATION MEAN ME in % |
|---|---|---|---|
| NORMALS PATIENTS | + | +* | ≥48 |
| ANOSMIA ∞ HYPOSMIA | 0 | 0 | 0 |
| TYPE I | ± | 0 | 0 |
| TYPE II | ± | ±* | <48 |

+ Normal ($\leq 10^{-5M}$ for all odorants)
+* Normal ($\leq 10^{-2M}$ for all odorants)
0 Absent response (∞)
+ Present but < normal ($>10^{-5M}<\infty$ for all odorants)
±* Present but < normal ($>10^{-2M}<\infty$ for all odorants)
∞ Inability to detect, recognize or judge intensity of an absolute concentration of odorant After determination of hyposmia, patients were treated in an open label, fixed design, controlled open trial. Patients were given an oral extended release theophylline in divided daily doses taken in the middle of breakfast and lunch. All patients were initially given 200 mg of theophylline; changes in this dose were made based upon subjective responses to therapy. If at a subsequent return visit, patients reported ≥5% subjective improvement in overall smell function, they continued on this same dose of theophylline and were reevaluated after four to six months of continued treatment. Results from any subsequent return from these improved patients were not included in any subsequent data report. All subsequent comparisons between treated and untreated patients were made only between those patients continuing in the study compared to their own measurements obtained in the untreated state. If patients reported <5% subjective improvement, their theophylline dose was increased by 200 mg daily and they were scheduled for retesting at the study site after two to four months at this new dosage. For patients that reported <5% improvement, this sequence continued until patients reached 800 mg of theophylline, at which time the study was considered completed.

Patients were initially divided into two groups based upon proximity to the study site. One group, consisting of local patients (212 patients), returned for reevaluation after two-four months of treatment. The other group, consisting of distant patients (100 patients), called the study site at two to four month intervals and visited the study site after six to 10 months of treatment. Some of the distant patients returned after treatment on 200 mg, 400 mg, 600 mg of theophylline and these results were included with those of local patients at each dose level (see FIG. 1 for patient details).

Local Patients—First Return (200 mg Theophylline)

Patients returned for reevaluation after two to four months of treatment. Measurements of blood serum theophylline were measured by a fluorescence polarization assay (Abbott, Chicago, Ill.). At this time, subjective changes in smell function were measured independently (compared to patient's memory of previous normal smell function monitored by use of the patients' daily measurements) using the scale from −100–0∓100 previously described (vs). After independently recording their subjective responses, smell function was measured for all four odors with DT, RT, ME and H determined without recourse to prior measurements.

Local Patients—Second Return (400 mg Theophylline)

Patients returned after four to eight months of treatment and consisted of patients who previously reported <5% improvement on 200 mg of theophylline but also some distant patients who returned on this dose. Blood theophylline was measured as before. All patients independently reported subjective overall changes in smell function as done previously. At this visit, smell function was measured as before to determine DT, RT, ME and H for all four odors without recourse to prior measurements.

Local Patients—Third Return (600 mg Theophylline)

Patients returned after four-10 months of treatment and included both patients who reported <5% improvement on 400 mg theophylline and also some of the distant patient group. Blood theophylline was obtained as before. Patients independently reported subjective changes in overall smell function and measurements of DT, RT, ME and H were obtained as before for all four odors without recourse to prior measurements.

Local Patients—Fourth Return (800 mg Theophylline)

Patients returned after four-eight months of treatment and included patients who reported <5% improvement on 600 mg theophylline and also some of the distant patient group. Blood theophylline was obtained as before. Patients independently reported subjective changes in overall smell function and measurements of DT, RT, ME and H were obtained as before for all four odors without recourse to prior measurements.

Distant Patients—First Call in (200 mg Theophylline)

Subjective overall changes in smell acuity were reported by telephone and by FAX or email at two-four month intervals after treatment was initiated using the standardized form in which they measured daily changes in smell acuity using the −100–0±100 scale as noted above (vs). Using the same criteria noted above, if at their initial two-four month call-in they reported improvement in smell acuity of >5%, they continued at 200 mg and returned to the study site at four-six months on this treatment dose. If they reported improvement in smell acuity of <5% their dose of theophylline was increased to 400 mg for an additional two-four months and they then called the study site at the end of this period.

Distant Patients—Second Call in (400 mg Theophylline)

At this time, if patients reported >5% improvement on 400 mg they continued on this dose and returned to the study site after four-six months on this treatment dose. If they reported <5% improvement in smell function their theophylline dose was increased to 600 mg and they then called the study site after four-six months on this treatment dose.

Distant Patients—Third Call in (600 mg Theophylline)

At this time, if patients reported ≥5% improvement they were continued on this treatment dose and were requested to return to the study site in four-six months. If they reported <5% improvement in smell function they were requested to return to the study site as soon as possible to reevaluate their smell function. At this return, blood theophylline levels were measured. Smell function was measured using the subjective and psychophysical techniques (DT, RT, ME, H) previously described.

Distant Patients—Fourth Call in (800 mg Theophylline)

At this time, if patients reported either ≥5% improvement or <5% improvement, they were requested to return to the study site as soon as possible to reevaluate their smell function. At this return, blood theophylline levels were measured and smell function were measured using both subjective and psychophysical techniques with results as shown on Table VII and discussed previously.

Since data for all measurements from each patient group (local or distant) on each dose level were combined mean and SEM for each measurement (DT, RT, ME, H) of smell function for each treatment group were calculated on this basis. Differences in measurements between before treatment and each treatment level were calculated and significance of differences estimated using Student t tests (values $p<0.05$ considered significant). Some patient responses were also analyzed by use of non-parametric statistics (sign test) and the Spearman rank correlation technique; $r<0.05$ was considered significant related to smell loss type and treatment response. Since each patient served as his/her own control with respect to before and after treatment, paired t tests were also calculated; t values <0.05 were considered significant. These values were not included in the results presented.

Results were previously obtained in 150 normal subjects for each of these measurements (1, 53-55) and are reported here for comparison.

Results

Figure 2A:
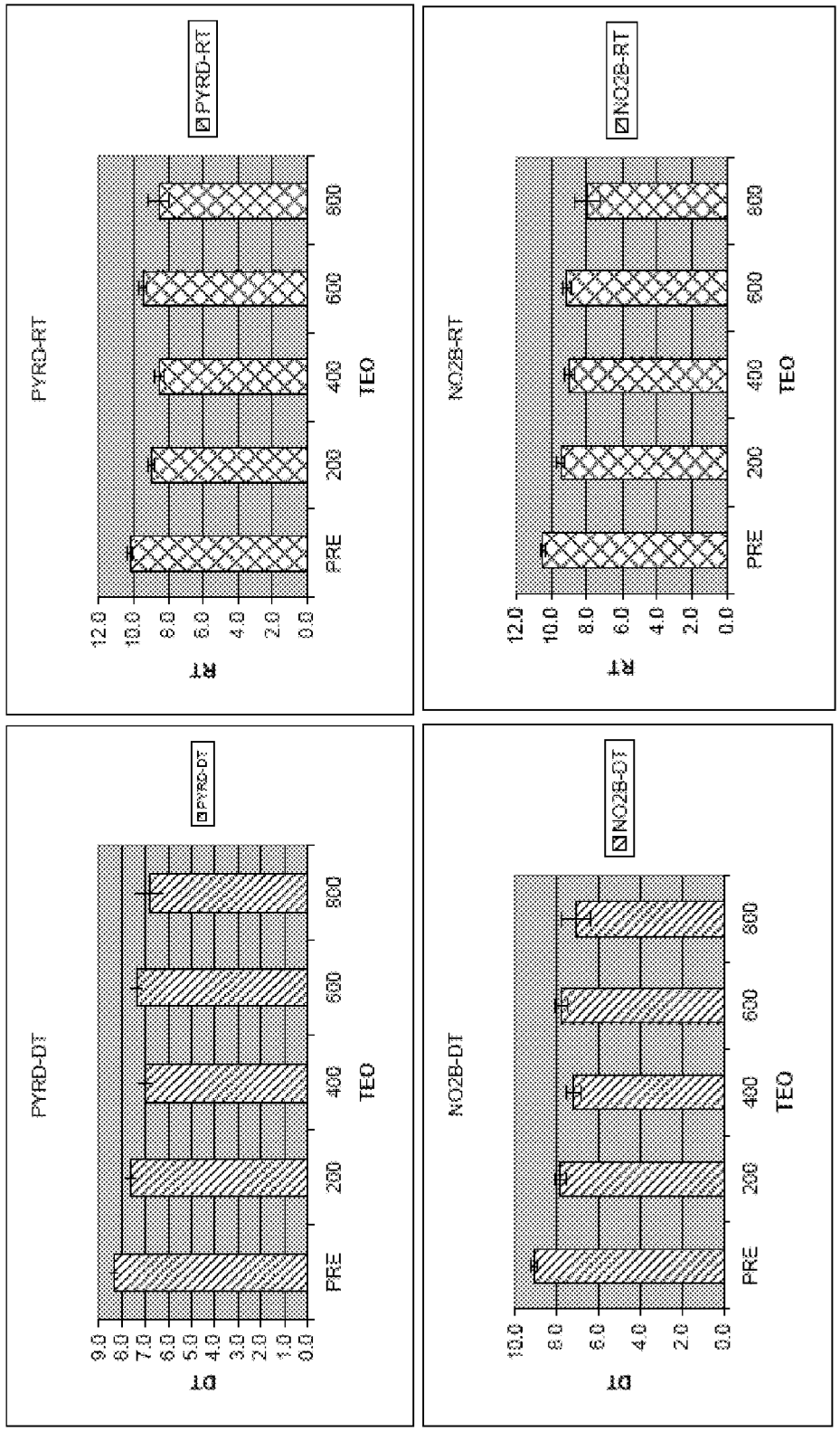
FIG. 2A-B is a comparison of DT and RT values for pyridine (PYRD), nitrobenzene (NO2B), thiophene (THIO) and amyl acetate (AA) in 312 patients before treatment and in all patients in each group after treatment with oral theophylline at 200 mg, 400 mg, 600 mg and 800 mg (see Tables II, IV-VII).
Figure 2B:
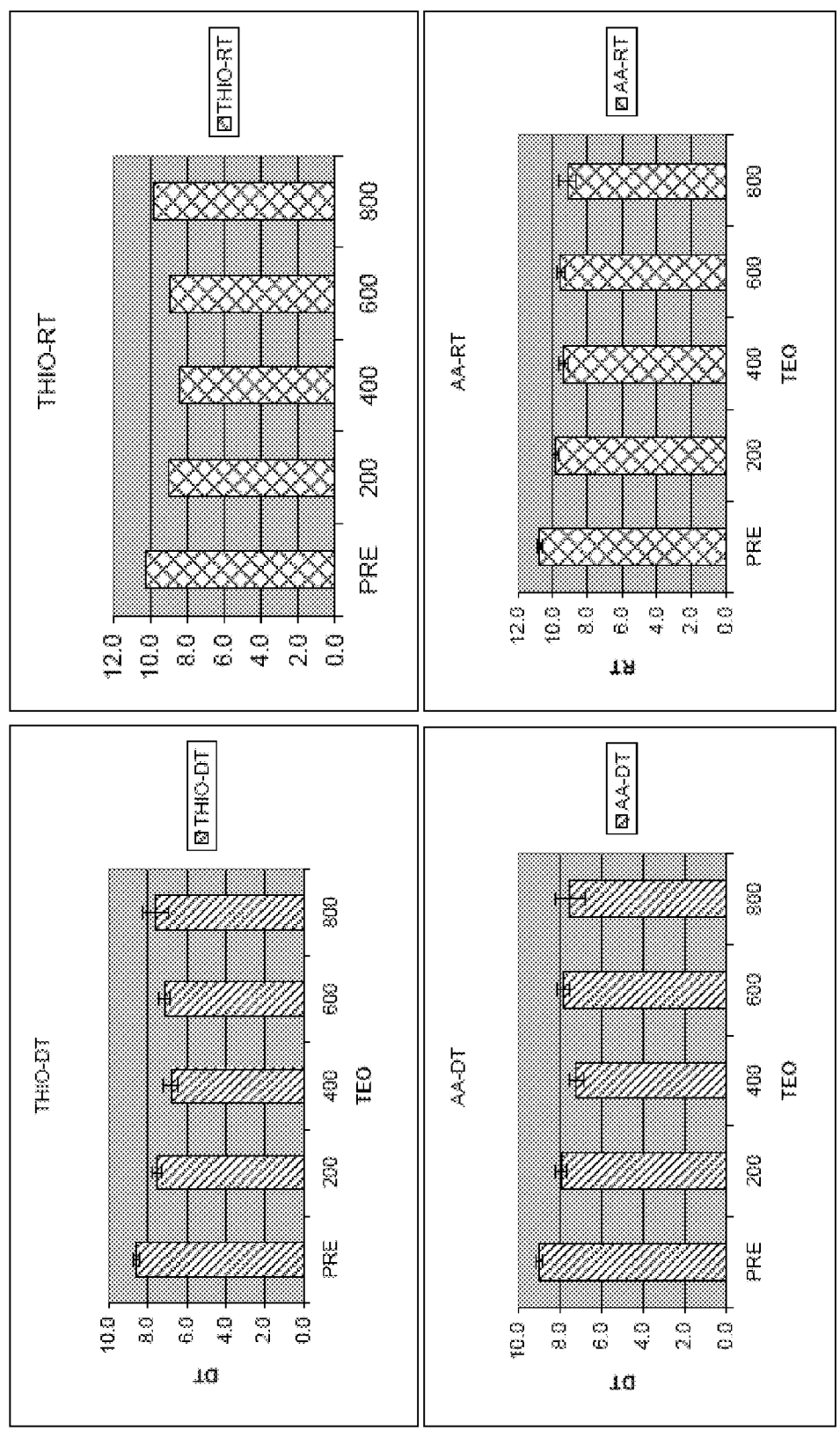

Comparison of Smell Function in Normal Subjects and in Untreated Patients with Hyposmia Results of each measurement (DT, RT, ME and H) in untreated patients indicated significant impairment of smell function compared to normal subjects (Table II, FIG. 2A-B). For DT and RT, patient responses were significantly higher (less sensitive) than in normals (Table II), ME responses were significantly lower (less sensitive) than in normals (FIG. 2A-B). H responses were significantly lower (less pleasant) for amyl acetate and nitrobenzene (odors usually considered pleasant) and significantly higher for pyridine and thiophene (less unpleasant—closer to zero for odors usually considered unpleasant) (FIG. 2A-B). Analysis of H data indicate that for normal subjects H values for pyridine and thiophene (unpleasant responses) are similar to or slightly higher than ME values, whereas H values for nitrobenzene and amyl acetate (pleasant responses) are similar or slightly lower. Ratios of H:ME in normals for pyridine and thiophene are 1.09 and 1.05 whereas for nitrobenzene and amyl acetate they are 0.94 and 0.96. For untreated patients (patients with Type II and III hyposmia only) these ratios are quite different. For pyridine and thiophene, these ratios are 0.87 and 0.81 whereas for nitrobenzene and amyl acetate they are 0.81 and 0.10. In part, H decreases for nitrobenzene and amyl acetate are related to decreased patient acuity; however, the major discrepancy is that about 50% of patients with hyposmia also exhibit dysosmia (1, 2) in which odors usually considered pleasant are considered unpleasant (e.g., banana-oil odor may be considered putrid) and even unpleasant odors may be considered pleasant (e.g., pyridine may be considered flowery). These distortions in patients comprise a bimodal response for H values (some patients reporting a normal hedonic response related to appropriate pleasantness and unpleasantness of the perceived odor whereas others reporting a distortion) which reduces the overall arithmetic mean obtained for H for each odor.

TABLE II

DIFFERENCES IN SMELL FUNCTION BETWEEN STUDY PATIENTS BEFORE TREATMENT AND NORMAL CONTROLS

| SMELL FUNCTION\ODOR | PATIENTS (312) | | | | NORMALS (155) | | | |
|---|---|---|---|---|---|---|---|---|
| | PYRD | NO$_2$B | THIO | AA | PYRD | NO$_2$B | THIO | AA |
| DT | 8.5 ± 0.2*,$^a$ | 9.0 ± 0.2$^a$ | 8.5 ± 0.2$^a$ | 8.9 ± 0.2$^a$ | 4.2 ± 0.1 | 3.9 ± 0.1 | 3.6 ± 0.1 | 3.7 ± 0.1 |
| RT | 10.2 ± 0.1$^a$ | 10.5 ± 0.2$^a$ | 10.2 ± 0.2$^a$ | 10.7 ± 0.01$^a$ | 7.2 ± 0.1 | 5.7 ± 0.1 | 7.1 ± 0.1 | 6.8 ± 0.1 |
| ME | 23 ± 2$^a$ | 12 ± 1$^a$ | 16 ± 2$^a$ | 10 ± 1$^a$ | 64 ± 3 | 51 ± 4 | 66 ± 4 | 51 ± 4 |
| H | −20 ± 2$^a$ | 4 ± 1$^a$ | −13 ± 2$^a$ | 1 ± 1$^a$ | −74 ± 3 | 48 ± 5 | −80 ± 2 | 54 ± 5 |

( ) Patient number
*Mean ± SEM
DT, detection threshold, in bottle units [BU ( )]
RT, recognition threshold, in bottle units [BU ( )]
ME, magnitude estimation, in % ( )
H, hedonic estimation, in % (+, pleasant, −, unpleasant, 0, neutral)
PYRD, pyridine;
NO$_2$B, nitrobenzene;
THIO, thiophene;
AA, amyl acetate
With respect to normals
$^a$p < 0.001

Comparison of Smell Function in Patients Classified by Degree of Smell Loss

Categorized by smell loss type, results of each measurement indicate that before treatment, patients exhibited a consistent pattern of abnormality associated with their loss type such that Type I hyposmia>Type II>Type III (Table III). H:ME ratios were closer to those of normals in patients with Type III compared to those with Type II hyposmia, as would be expected due to the lesser degree of abnormality in the former patients (Table III).

Figure 3A:
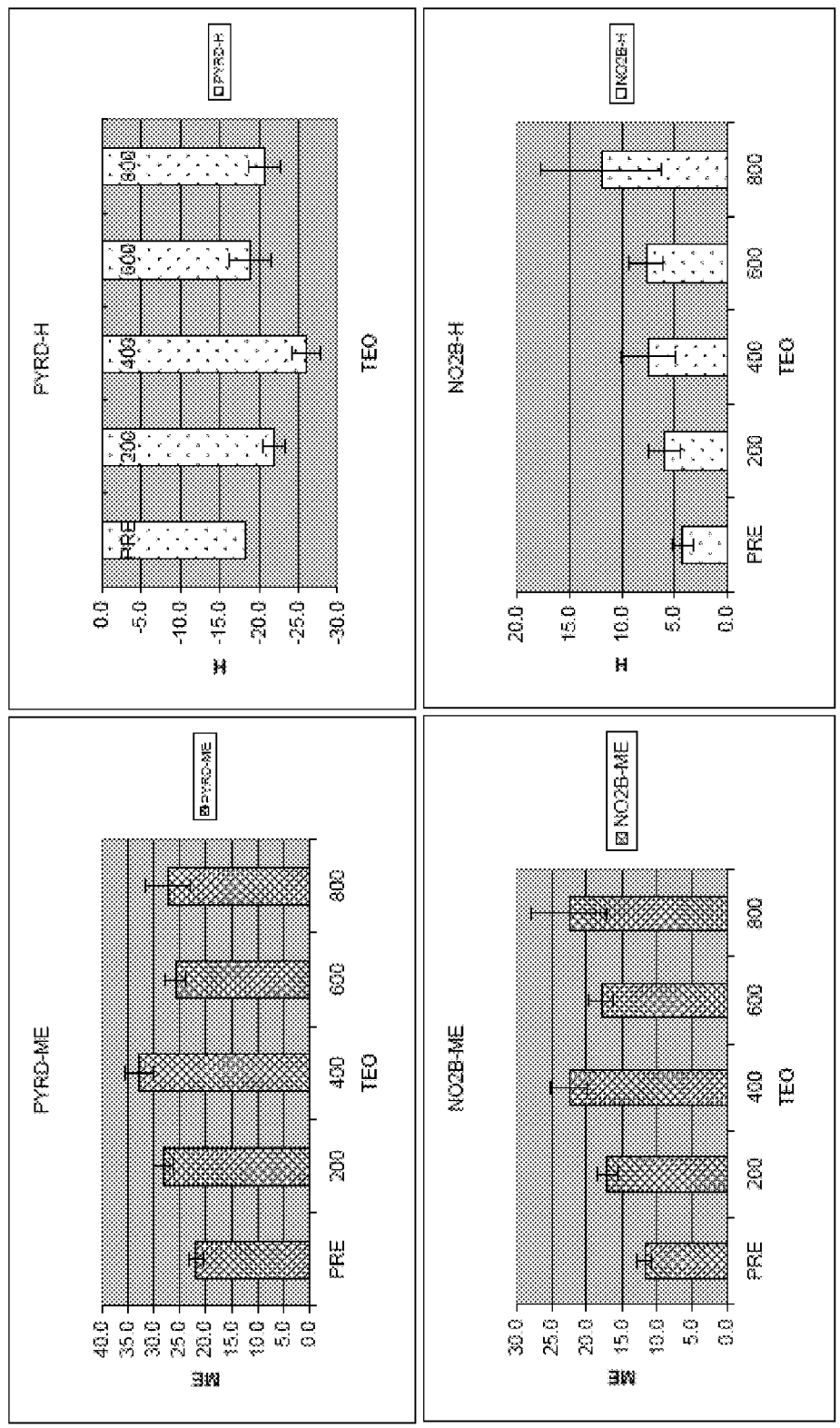
FIG. 3A-B is a comparison of ME and H values for pyridine (PYRD), nitrobenzene (NO2B), thiophene (THIO) and amyl acetate (AA) in 312 patients before treatment and in all patients in each group after treatment with oral theophylline at 200 mg, 400 mg, 600 mg and 800 mg (see Tables II, IV-VII).
Figure 3B:
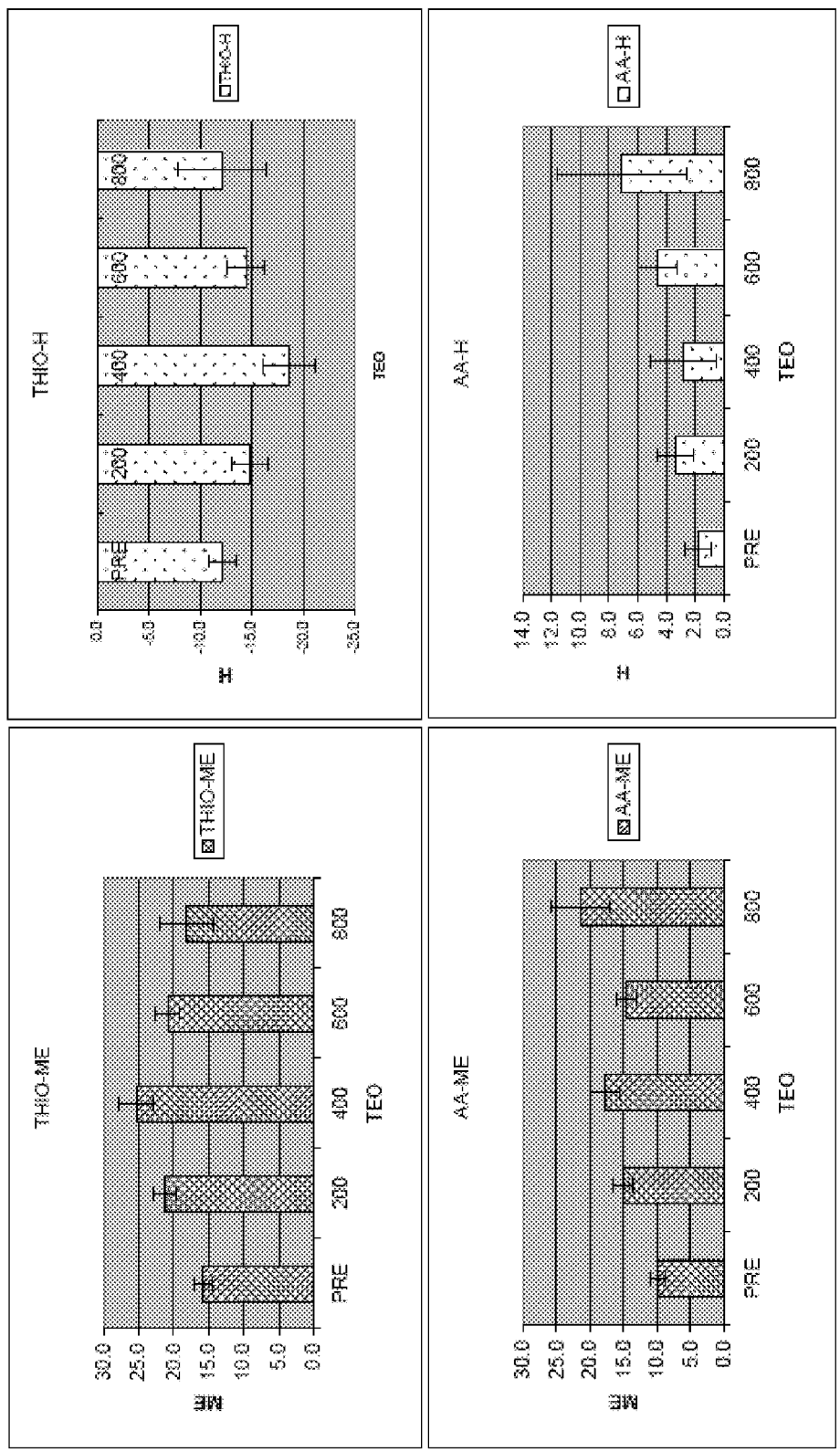

Changes in Smell Function in All Patients Treated with Theophylline, 200 mg Daily Changes in smell function in 199 patients with hyposmia after treatment with 200 mg daily of theophylline for two-six months are shown in Table IV and in FIG. 3A-B. These patients constituted mainly local patients minus 15 of the original 312 who did not return after treatment was initiated. Of the 15 non-returning patients, seven reported >5% improvement (46.7%) and one (14.3%) reported a return to normal; eight reported improvement of <5%. With returning patients, 34 patients (17.1%) improved ≥5% (and were not included in subsequent studies). Among this group nine

TABLE III

COMPARISON OF SMELL FUNCTION BETWEEN UNTREATED PATIENTS WITH TYPES I, II AND III HYPOSMIA

| | I (96) | | | | II (208) | | | |
|---|---|---|---|---|---|---|---|---|
| | PYRD | NO$_2$B | THIO | AA | PRYD | NO$_2$B | THIO | AA |
| DT | 9.8 ± 0.1* | 11.2 ± 0.2 | 10.9 ± 0.2 | 11.7 ± 0.2 | 8.8 ± 0.2 | 8.3 ± 0.2$^a$ | 8.0 ± 0.2$^a$ | 8.2 ± 0.2$^a$ |
| RT | 11.7 ± 0.1 | 11.8 ± 0.1 | 11.8 ± 0.1 | 11.8 ± 0.1 | 9.7 ± 0.1$^a$ | 10.1 ± 0.2$^a$ | 9.7 ± 0.2$^a$ | 10.4 ± 0.2$^a$ |
| ME | 0 | 0 | 0 | 0 | 29 ± 2$^a$ | 16 ± 1$^a$ | 21 ± 2$^a$ | 13 ± 1$^a$ |
| H | 0 | 0 | 0 | 0 | −25 ± 2$^a$ | 5 ± 1$^a$ | −16 ± 2$^a$ | 1 ± 1 |

| | | | | | III (8) | | | |
|---|---|---|---|---|---|---|---|---|
| | | | | | PRYD | NO$_2$B | THIO | AA |
| DT | | | | | 4.0 ± 0.5 | 3.4 ± 0.6$^{a,a1}$ | 3.3 ± 0.8$^{a,a1}$ | 2.5 ± 0.5$^{a,a1}$ |
| RT | | | | | 5.6 ± 0.8 | 4.0 ± 0.9$^{a,a1}$ | 3.9 ± 0.8$^{a,a1}$ | 5.3 ± 1.0 |
| ME | | | | | 42 ± 4$^{a,a1}$ | 34 ± 4$^{a,a1}$ | 34 ± 10$^a$ | 40 ± 2$^{a,a1}$ |
| H | | | | | −27 ± 14$^a$ | 12 ± 7$^a$ | −46 ± 13$^a$ | 34 ± 6$^{a,a1}$ |

( ) Patient number
* Mean ± SEM
DT, detection threshold, in BU
RT, recognition threshold, in BU
ME, magnitude estimation, in %
H, hedonic estimation, in %
PYRD, pyridine;
NO$_2$B, nitrobenzene;
THIO, thiophene;
AA, amyl acetate
With respect to Type I
$^a$p < 0.001
With respect to Type II
$^{a1}$p < 0.001

(26.5%) considered their smell function had returned to normal. Two hundred sixty-three patients improved <5% (160 local and 103 distant patients); among this group 36 patients did not continue in the study.

Among the 199 patients (both improved and not improved) who returned on 200 mg, DT and RT for all odors decreased (improved) significantly (Table IV). ME for pyridine and amyl acetate also increased (improved) significantly (FIG. 3A-B). H values for pyridine and thiophene decreased significantly [i.e., odors pyridine and thiophene were recognized as more unpleasant (FIG. 3A-B)] and H values for nitrobenzene increased significantly [i.e., the odor of nitrobenzene was recognized as more pleasant (FIG. 3A)]. While not statistically significant, H values for amyl acetate increased 50% (perceived as more pleasant with improved odor recognition). On treatment, H:ME ratios did not change significantly since both ME and H values changed to similar degrees. No differences in results with respect to age or gender of these patients were apparent. At subsequent visits over the next six-36 months with continued treatment on this dose, the 34 patients with initially improved smell function maintained their increased acuity or improved further. Mean serum theophylline on this treatment was 4.0±0.2 mg/dl.

time on 400 mg) were reevaluated after taking 400 mg of theophylline for two-six months (Table IV). On this treatment dose, 35 patients (29.2%) improved ≥5% (and were not included in subsequent studies). Among this group, three (8.6%) considered their smell function had returned to normal. One hundred ninety-two patients improved <5% (96 local and 96 distant patients). Twenty-five patients of these 192 did not continue in the study. On this dose, DT and RT for all odors decreased (improved) significantly and ME for all odors increased (improved) significantly (Table V) (both improved and unimproved patients included). Hedonic values also increased significantly for pyridine and thiophene [i.e., odors of pyridine and thiophene were recognized as more unpleasant (FIG. 2A-B)]. While not statistically significant, H values for nitrobenzene increased 50% (perceived as more pleasant); H values for thiophene decreased 40% (perceived as more unpleasant). Overall, H:ME ratios did not change significantly on treatment. No differences in results with respect to age or gender of these patients were apparent.

TABLE IV

CHANGES IN SMELL FUNCTION FOLLOWING TREATMENT WITH ORAL THEOPHYLLINE, 200 MG DAILY

| SMELL FUNCTION\ODOR | Before Treatment (199) | | | | After Treatment (199) | | | |
|---|---|---|---|---|---|---|---|---|
| | PYRD | NO$_2$B | THIO | AA | PYRD | NO$_2$B | THIO | AA |
| DT | 8.5 ± 0.2* | 9.0 ± 0.2 | 8.5 ± 0.2 | 8.9 ± 0.2 | 7.6 ± 0.2$^a$ | 7.8 ± 0.2$^d$ | 7.5 ± 0.2$^c$ | 7.9 ± 0.2$^c$ |
| RT | 10.2 ± 0.1 | 10.5 ± 0.2 | 10.2 ± 0.2 | 10.7 ± 0.1 | 9.0 ± 0.2$^a$ | 9.5 ± 0.2$^a$ | 9.1 ± 0.2$^c$ | 9.9 ± 0.2$^c$ |
| ME | 23 ± 2 | 12 ± 1 | 16 ± 2 | 10 ± 1 | 28 ± 2$^a$ | 17 ± 2 | 21 ± 2 | 15 ± 2$^d$ |

( ) Patient number
*Mean ± SEM
DT, detection threshold, in BU
RT, recognition threshold, in BU
ME, magnitude estimation, in %
H, hedonic estimation, in %
PYRD, pyridine;
NO$_2$B, nitrobenzene;
THIO, thiophene;
AA, amyl acetate
With respect to before treatment
$^a$p < 0.001
$^b$p < 0.005
$^c$p < 0.01
$^d$p < 0.05

Changes in Smell Function in Patients with Hyposmia Treated with Theophylline 400 mg Daily One hundred twenty patients (97 from the 165 who returned on <5% on 200 mg and 23 who returned for the first Among patients who exhibited improvement at this dose, on subsequent visits over six-36 months, their improvement persisted. Mean serum theophylline on this treatment dose was 7.4±0.4 mg/dl.

TABLE V

CHANGES IN SMELL FUNCTION FOLLOWING TREATMENT WITH ORAL THEOPHYLLINE, 400 MG DAILY

| SMELL FUNCTION\ODOR | Before Treatment (120) | | | | After Treatment (120) | | | |
|---|---|---|---|---|---|---|---|---|
| | PYRD | NO$_2$B | THIO | AA | PYRD | NO$_2$B | THIO | AA |
| DT | 8.4 ± 0.2* | 9.0 ± 0.3 | 8.6 ± 0.3 | 8.9 ± 0.3 | 7.0 ± 0.3$^c$ | 7.2 ± 0.3$^c$ | 6.8 ± 0.4$^c$ | 7.1 ± 0.3$^b$ |
| RT | 10.3 ± 0.2 | 10.5 ± 0.2 | 10.5 ± 0.2 | 10.6 ± 0.2 | 8.5 ± 0.3$^a$ | 8.9 ± 0.3$^b$ | 8.4 ± 0.3$^a$ | 9.3 ± 0.3$^b$ |

TABLE V-continued

CHANGES IN SMELL FUNCTION FOLLOWING TREATMENT WITH ORAL THEOPHYLLINE, 400 MG DAILY

| SMELL FUNCTION\ODOR | Before Treatment (120) | | | | After Treatment (120) | | | |
|---|---|---|---|---|---|---|---|---|
| | PYRD | NO$_2$B | THIO | AA | PYRD | NO$_2$B | THIO | AA |
| ME | 21 ± 2 | 12 ± 2 | 14 ± 2 | 10 ± 1 | 33 ± 3$^a$ | 23 ± 2$^a$ | 26 ± 2$^c$ | 18 ± 2$^c$ |
| H | −19 ± 2 | 4 ± 1 | −12 ± 2 | 2 ± 1 | −26 ± 3$^b$ | 8 ± 3$^a$ | −19 ± 2$^d$ | 3 ± 2 |

( ) Patient number
*Mean ± SEM
DT, detection threshold, in BU
RT, recognition threshold, in BU
ME, magnitude estimation, in %
H, hedonic estimation, in %
PYRD, pyridine;
NO$_2$B, nitrobenzene;
THIO, thiophene;
AA, amyl acetate
With respect to before treatment
$^a$p < 0.001
$^b$p < 0.005
$^c$p < 0.01
$^d$p < 0.05

Change in Smell Function in Patients with Hyposmia Treated with Theophylline, 600 mg Daily Changes in smell function in 160 patients after treatment with 600 mg daily for two-12 months are shown on Table VI. This patient number includes 77 distant patients who returned more pleasant (FIG. 3A-B). Overall, H:ME ratios did not change significantly. Again, as noted on the previous theophylline doses, no differences were apparent with respect to age or gender of these patients. Mean serum theophylline on this dose was 9.4±0.38 mg/dl.

TABLE VI

CHANGES IN SMELL FUNCTION FOLLOWING TREATMENT WITH ORAL THEOPHYLLINE, 600 MG DAILY

| SMELL FUNCTION\ODOR | Before Treatment (160) | | | | After Treatment (160) | | | |
|---|---|---|---|---|---|---|---|---|
| | PYRD | NO$_2$B | THIO | AA | PYRD | NO$_2$B | THIO | AA |
| DT | 8.4 ± 0.2* | 9.2 ± 0.2 | 8.8 ± 0.2 | 9.3 ± 0.2 | 7.4 ± 0.2$^c$ | 7.8 ± 0.3$^a$ | 7.1 ± 0.3$^a$ | 7.8 ± 0.3$^a$ |
| RT | 10.3 ± 0.2 | 10.5 ± 0.2 | 10.3 ± 0.2 | 10.8 ± 0.2 | 9.4 ± 0.2$^c$ | 9.1 ± 0.2$^c$ | 9.0 ± 0.3$^c$ | 9.6 ± 0.2$^a$ |
| ME | 19 ± 2 | 11 ± 1 | 13 ± 2 | 8 ± 1 | 26 ± 2$^d$ | 18 ± 2$^d$ | 21 ± 2$^d$ | 15 ± 2$^c$ |
| H | −16 ± 2 | 3 ± 1 | −9 ± 2 | 2 ± 1 | −19 ± 2 | 8 ± 2$^d$ | −14 ± 2 | 4 ± 1 |

( ) Patient number
*Mean ± SEM
DT, detection threshold, in BU
RT, recognition threshold, in BU
ME, magnitude estimation, in %
H, hedonic estimation, in %
PYRD, pyridine;
NO$_2$B, nitrobenzene;
THIO, thiophene;
AA, amyl acetate
With respect to before treatment
$^a$p < 0.001
$^b$p < 0.005
$^c$p < 0.01
$^d$p < 0.05 on this theophylline dose as well as 83 local patients who improved <5% on 400 mg. Among this group, 66 (41.2%) improved ≥5% and 17 (10.6%) considered their smell function had returned to normal. On subsequent visits, over the next six-36 months, improvement on this dose either persisted or improved further. One hundred thirty-seven patients improved <5% and 73 did not continue. On this dose, DT and RT for all odors decreased (improved) significantly and ME for all odors increased (improved) significantly (Table VI) (both improved and unimproved patients included). H values did not change significantly for any odor, although pyridine and thiophene were recognized as more unpleasant (FIG. 3A-B) and nitrobenzene and amyl acetate were recognized as more pleasant (FIG. 3A-B). Overall, H:ME ratios did not Change in Smell Function in Patients with Hyposmia Treated with Theophylline, 800 mg Daily Changes in smell function in 28 patients after treatment with 800 mg daily for two-12 months are shown in Table VII. Among this group, 15 (53.6%) improved ≥5% and three (33%) considered their smell function had returned to normal. On subsequent visits over the next two-six months, improvement on this dose persisted or improved further. Thirteen patients improved <5%. At this dose, the study terminated. DT and RT for all odors increased on treatment, but were statistically significant only for DT for nitrobenzene, RT for nitrobenzene and amyl acetate. ME for all odors increased, but was significant only for amyl acetate. H for both pyridine and thiophene decreased 55% and 37%, respectively (became more unpleasant) and H for nitrobenzene and amyl acetate increased about 50% (became more pleasant). When analyzed by paired t test (data not shown) DT, RT and ME for all odors increased significantly, H for pyridine and thiophene decreased significantly and H for nitrobenzene and amyl acetate increased significantly. Mean serum theophylline on this dose was 11.2±0.8 mg/dl.

As drug doses increased mean DT and RT for most odors decreased (acuity increased) whereas, mean ME for most odors increased from 200 mg to 400 mg and then remained relatively constant. H also decreased from 200 mg to 400 mg (increased unpleasantness) for pyridine and thiophene and then remained relatively constant as doses increased; H for nitrobenzene and amyl acetate (increased pleasantness) increased in a similar manner.

TABLE VII

CHANGES IN SMELL FUNCTION FOLLOWING TREATMENT WITH ORAL THEOPHYLLINE, 800 MG DAILY

| SMELL | Before Treatment (28) | | | | After Treatment (28) | | | |
|---|---|---|---|---|---|---|---|---|
| FUNCTION\ODOR | PYRD | NO$_2$B | THIO | AA | PYRD | NO$_2$B | THIO | AA |
| DT | 7.9 ± 0.6* | 9.3 ± 0.7 | 8.9 ± 0.6 | 8.8 ± 0.7 | 6.9 ± 0.6 | 7.0 ± 0.8$^d$ | 7.2 ± 0.7 | 7.2 ± 0.8 |
| RT | 10.6 ± 0.3 | 10.1 ± 0.6 | 10.2 ± 0.5 | 10.9 ± 0.3 | 8.5 ± 0.6$^c$ | 7.8 ± 0.8$^d$ | 9.6 ± 0.6 | 9.0 ± 0.5$^b$ |
| ME | 18 ± 4 | 11 ± 4 | 14 ± 4 | 10 ± 4 | 29 ± 5 | 25 ± 6 | 20 ± 4 | 24 ± 2$^a$ |
| H | −12 ± 4 | 6 ± 2 | −9 ± 4 | 4 ± 4 | −22 ± 6 | 13 ± 7 | −15 ± 4 | 8 ± 5 |

( ) Patient number
*Mean ± SEM
DT, detection threshold, in BU
RT, recognition threshold, in BU
ME, magnitude estimation, in %
H, hedonic estimation, in %
PYRD, pyridine;
NO$_2$B, nitrobenzene;
THIO, thiophene;
AA, amyl acetate
With respect to before treatment
$^a$p < 0.001
$^b$p < 0.005
$^c$p < 0.01
$^d$p < 0.05

Changes in Smell Function and after Treatment with Theophylline in Patients Classified by Hyposmia Type Type I Hyposmia Treatment. After treatment with either 200 mg, 400 mg, 600 mg or 800 mg, there were significant decreases in DT and RT, increases in ME and changes in H for specific odors consistent with improvement in smell function (Table VIII). Of the 96 patients with Type I hyposmia in the study, 32 (33.3%) reported >5% improvement and 5 (15.6%) reported their smell function had returned to normal.

TABLE VIII

CHANGES IN SMELL FUNCTION IN TYPE I HYPOSMIA PATIENTS FOLLOWING TREATMENT

| SMELL | Before Treatment (96) | | | | | | | |
|---|---|---|---|---|---|---|---|---|
| FUNCTION\ODOR | PYRD | NO$_2$B | THIO | AA | PYRD | NO$_2$B | THIO | AA |
| | | | | | After Treatment 200 mg (57) | | | |
| DT | 9.8 ± 0.1* | 11.2 ± 0.2 | 10.9 ± 0.2 | 11.2 ± 0.2 | 9.5 ± 0.2 | 10.3 ± 0.3$^a$ | 10.1 ± 0.3$^d$ | 10.5 ± 0.3$^d$ |
| RT | 11.7 ± 0.1 | 11.8 ± 0.1 | 11.8 ± 0.1 | 11.7 ± 0.1 | 11.0 ± 0.2$^a$ | 11.2 ± 0.2$^d$ | 11.4 ± 0.2 | 11.3 ± 0.2 |
| ME | 0 | 0 | 0 | 0 | 11 ± 2$^a$ | 5 ± 2$^a$ | 6 ± 2$^a$ | 6 ± 2$^a$ |
| H | 0 | 0 | 0 | 0 | −8 ± 2$^a$ | 4 ± 2$^a$ | −3 ± 2$^a$ | 4 ± 2$^a$ |
| | | | | | After Treatment 400 mg (33) | | | |
| DT | | | | | 8.8 ± 0.5 | 9.8 ± 0.5$^a$ | 9.8 ± 0.5$^a$ | 10.1 ± 0.5$^a$ |
| RT | | | | | 10.6 ± 0.4 | 10.9 ± 0.4$^e$ | 10.8 ± 0.4$^d$ | 11.2 ± 0.3 |
| ME | | | | | 12 ± 3$^a$ | 8 ± 3$^a$ | 7 ± 2$^a$ | 7 ± 3$^a$ |
| H | | | | | −7 ± 3$^a$ | 3 ± 3$^a$ | −5 ± 2$^a$ | 5 ± 3$^a$ |
| | | | | | After Treatment 600 mg (51) | | | |
| DT | | | | | 8.9 ± 0.3$^b$ | 9.9 ± 0.4$^c$ | 9.4 ± 0.4$^a$ | 10.1 ± 0.3$^a$ |
| RT | | | | | 10.9 ± 0.3 | 10.8 ± 0.3$^e$ | 10.9 ± 0.3$^b$ | 11.1 ± 0.2$^c$ |
| ME | | | | | 11 ± 3$^a$ | 6 ± 2$^a$ | 7 ± 2$^a$ | 5 ± 2$^a$ |
| H | | | | | −8 ± 2$^a$ | 2 ± 2 | −3 ± 2$^a$ | −0.4 ± 1 |

TABLE VIII-continued

CHANGES IN SMELL FUNCTION IN TYPE I HYPOSMIA PATIENTS FOLLOWING TREATMENT

| SMELL FUNCTION\ODOR | Before Treatment (96) | | | | | | | |
|---|---|---|---|---|---|---|---|---|
| | PYRD | NO$_2$B | THIO | AA | PYRD | NO$_2$B | THIO | AA |
| | | | | | After Treatment 800 mg (12) | | | |
| DT | | | | | 9.6 ± 0.8 | 10.1 ± 0.8 | 10.0 ± 0.7 | 10.6 ± 0.5 |
| RT | | | | | 10.3 ± 1.0 | 11.3 ± 0.7 | 11.6 ± 0.2 | 11.6 ± 0.4 |
| ME | | | | | 10 ± 4$^a$ | 4 ± 3$^a$ | 4 ± 2$^a$ | 5 ± 3$^a$ |
| R | | | | | −11 ± 5$^a$ | 2 ± 2$^a$ | −4 ± 2$^a$ | −1 ± 4 |

( ) Patient number;
*Mean ± SEM
DT, detection threshold, in BU
RT, recognition threshold, in BU
ME, magnitude estimation, in %
H, hedonic value, in %
PYRD, pyridine;
NO$_2$B, nitrobenzene;
THIO, thiophene;
AA, amyl acetate
Compared to before treatment
$^a$p < 0.001
$^b$p < 0.005
$^c$p < 0.01
$^d$p < 0.05

Type II Hyposmia Treatment. After treatment with either 200 mg, 400 mg, 600 mg or 800 mg, there were significant decreases in DT and RT, increases in ME and changes in H for specific odor consistent with improvement in smell function (Table IX). Of the 208 patients with Type II hyposmia in the study, 129 (62%) reported >5% improvement and 26 (20.2%) reported their smell function had returned to normal.

TABLE IX

CHANGES IN SMELL FUNCTION IN TYPE II HYPOSMIA PATIENTS FOLLOWING TREATMENT

| SMELL FUNCTION\ODOR | Before Treatment (208) | | | | | | | |
|---|---|---|---|---|---|---|---|---|
| | PYRD | NO$_2$B | THIO | AA | PYRD | NO$_2$B | THIO | AA |
| | | | | | After Treatment 200 mg (138) | | | |
| DT | 8.8 ± 0.2 | 8.3 ± 0.2 | 8.0 ± 0.2 | 8.2 ± 0.2 | 6.9 ± 0.2 | 6.9 ± 0.3$^a$ | 6.5 ± 0.3 | 7.0 ± 0.3 |
| RT | 9.7 ± 0.1 | 10.1 ± 0.2 | 9.7 ± 0.2 | 10.4 ± 0.2 | 8.2 ± 0.2$^a$ | 8.8 ± 0.3 | 8.2 ± 0.3$^a$ | 9.3 ± 0.2 |
| ME | 29 ± 2 | 16 ± 1 | 21 ± 2 | 13 ± 1 | 35 ± 2 | 22 ± 2 | 27 ± 2 | 19 ± 2 |
| H | −25 ± 2 | 5 ± 1 | −16 ± 2 | 1 ± 1 | −28 ± 2 | 7 ± 2 | −19 ± 2 | 3 ± 2 |
| | | | | | After Treatment 400 mg (85) | | | |
| DT | | | | | 6.3 ± 0.3$^a$ | 6.3 ± 0.4$^a$ | 5.7 ± 0.4 | 6.1 ± 0.4$^a$ |
| RT | | | | | 7.7 ± 0.3$^a$ | 8.2 ± 0.4$^a$ | 7.6 ± 0.4$^a$ | 8.8 ± 0.4$^a$ |
| ME | | | | | 41 ± 3$^a$ | 27 ± 3$^a$ | 31 ± 3 | 21 ± 3 |
| H | | | | | −34 ± 3 | 11 ± 3 | −23 ± 3 | 0.3 ± 2.8 |
| | | | | | After Treatment 600 mg (105) | | | |
| DT | | | | | 6.7 ± 0.3$^a$ | 6.8 ± 0.3$^a$ | 6.1 ± 0.3$^a$ | 6.8 ± 0.3$^a$ |
| RT | | | | | 8.9 ± 0.3 | 8.4 ± 0.3 | 8.1 ± 0.3$^a$ | 8.9 ± 0.3$^a$ |
| ME | | | | | 33 ± 2 | 24 ± 2 | 27 ± 2 | 19 ± 2 |
| H | | | | | −25 ± 3 | 11 ± 2 | −20 ± 2 | 7 ± 2 |
| | | | | | After Treatment 800 mg (16) | | | |
| DT | | | | | 4.7 ± 0.7$^a$ | 4.6 ± 0.9$^a$ | 4.9 ± 0.7$^a$ | 4.6 ± 0.7$^a$ |
| RT | | | | | 7.1 ± 0.7$^a$ | 5.1 ± 0.9$^a$ | 8.0 ± 1.0 | 7.1 ± 0.6$^a$ |

TABLE IX-continued

CHANGES IN SMELL FUNCTION IN TYPE II HYPOSMIA PATIENTS FOLLOWING TREATMENT

| SMELL | Before Treatment (208) | | | | | | | |
|---|---|---|---|---|---|---|---|---|
| FUNCTION\ODOR | PYRD | NO$_2$B | THIO | AA | PYRD | NO$_2$B | THIO | AA |
| ME | | | | | 43 ± 5$^e$ | 42 ± 8$^b$ | 33 ± 6 | 38 ± 6$^e$ |
| H | | | | | −31 ± 9 | 22 ± 11 | −24 ± 8 | 13 ± 9 |

( ) Patient number
DT, detection threshold, in BU
RT, recognition threshold, in BU
ME, magnitude estimation, in %
H, hedonic value, in %
PYRD, pyridine;
NO$_2$B, nitrobenzene;
THIO, thiophene;
AA, amyl acetate
Compared to before treatment
$^a$ < 0.001
$^b$p < 0.005
$^c$p < 0.02

Type III Hyposmia Treatment. After treatment with either 200 mg, 400 mg or 600 mg, there were no significant changes in DT or RT, since these values were not significantly different from normal before treatment. After treatment, there were changes in ME and H, but values were variable due to the small number of patients in each treatment series (Table X). Of the eight patients with Type III hyposmia in the study, 5 (62.5%) reported >5% improvement and 3 (60%) reported their smell function had returned to normal (see Table X).

study considered their smell function had returned to normal. Improvement in smell function, once occurred, persisted and sometimes continued to improve as long as treatment continued.

Initial studies were made at two-six month intervals after drug initiation. Subjective responses indicated that return of function was both time and dose related; patients reported little or no improvement before four-six weeks of treatment

TABLE X

CHANGES IN SMELL FUNCTION IN TYPE III HYPOSMIA PATIENTS FOLLOWING TREATMENT

| SMELL | Before Treatment (8) | | | | | | | |
|---|---|---|---|---|---|---|---|---|
| FUNCTION\ODOR | PYRD | NO$_2$B | THIO | AA | PYRD | NO$_2$B | THIO | AA |
| | | | | | After Treatment 200 mg (4) | | | |
| DT | 4.0 ± 0.5 | 3.4 ± 0.6 | 3.3 ± 0.8 | 2.5 ± 0.5 | 4.0 ± 0.6 | 3.8 ± 0.7 | 3.2 ± 0.8 | 2.8 ± 0.5 |
| RT | 5.6 ± 0.8 | 4.0 ± 0.9 | 3.9 ± 0.8 | 5.3 ± 1.0 | 5.2 ± 0.5 | 5.0 ± 0.6 | 3.8 ± 0.6 | 5.2 ± 1.6 |
| ME | 42 ± 4 | 34 ± 4 | 34 ± 10 | 40 ± 2 | 45 ± 11 | 33 ± 8 | 47 ± 15 | 32 ± 10 |
| H | −27 ± 14 | 12 ± 7 | −46 ± 13 | 34 ± 8 | −40 ± 13 | 13 ± 12 | −40 ± 18 | 14 ± 13 |
| | | | | | After Treatment 400 mg (2) | | | |
| DT | | | | | 5.0 | 2.5 | 1 | 2 |
| RT | | | | | 5.0 | 4.0 | 1 | 3 |
| ME | | | | | 45 | 79 | 99 | 75 |
| H | | | | | −40 | −62 | −99 | 75 |
| | | | | | After Treatment 600 mg (4) | | | |
| DT | | | | | 3.8 ± 0.9 | 3.8 ± 0.9 | 2.0 ± 1.0 | 2.5 ± 1.0 |
| RT | | | | | 5.5 ± 0.9 | 4.5 ± 1.3 | 3.8 ± 0.9 | 4.8 ± 1.7 |
| ME | | | | | 41 ± 15 | 33 ± 13 | 42 ± 20 | 31 ± 17 |
| H | | | | | −26 ± 22 | 12 ± 16 | −35 ± 24 | 28 ± 19 |

( ) Patient number
DT, detection threshold, in BU
RT, recognition threshold, in BU
ME, magnitude estimation, in %
H, hedonic value, in %
PYRD, pyridine;
NO$_2$B, nitrobenzene;
THIO, thiophene;
AA, amyl acetate Discussion These results indicate that 157 of the 312 patients in the study (50.3%) were responsive to treatment with theophylline. Of these, 34 (21.7%) considered their smell function returned to normal levels. Overall, 10.9% of all patients in the and reported greater improvement as doses increased to 400 mg and especially to 600 mg and 800 mg.

Patients with smell loss exhibited varying degrees of loss prior to treatment, however, improvement was noted in patients regardless of degree of loss. Patients with lesser degrees of smell loss (Type II and III hyposmia) exhibited more improvement with more patients reporting a return to normal smell function on treatment than those with a more severe degree of loss (Type I hyposmia). Indeed, in terms of percent patients reporting a return to normal function, twice as many patients with Type II and III hyposmia compared to Type I reported a return to normal function. These results are useful since smell loss degree is related to severity of biochemical changes (35) responsible for the loss. This result lends credence to the smell loss classification previously devised (1, 2, 56) and alerts physicians treating these patients that patients with a greater degree of smell loss require greater care and diligence with respect to successful treatment responses. Among patients who did not improve (those who responded <5% improvement), increasing the dose of theophylline further to 800 mg improved smell function further. In another group of patients who improved <5%, the addition of another PDE inhibitor (i.e., cilostazol) to their dose of 600 mg or 800 mg of theophylline improved smell function in an additional 15% of patients.

When analyzed with respect to changes in objective psychophysical measurements of smell function, mean values for DT and RT improved significantly for all odors for each theophylline dose, whether or not subjective improvement occurred (Tables IV, V, VI). These results indicate that treatment with theophylline improved standardized threshold measurements of sensory function, albeit, not enough to be perceived by the patients as significant. While mean DT and RT for all odors improved on treatment, none of these means reached the level of improvement exhibited by normal subjects (cf, Tables III, IV, V, VI).

When analyzed with respect to ME on 200 mg theophylline (Table IV), only responses to pyridine were significantly greater than prior to treatment. ME for each odor, however, increased with the total mean increase (5.1%) consistent with the overall reported subjective improvement among the successfully treated patients. On 400 mg theophylline (Table V), ME for each odor increased significantly with a total mean increase of 10.4%. On 600 mg theophylline (Table VI), ME for each odor also increased significantly with a total mean increase of 6.9%. These results are probably more consistent with patient subjective changes, since most patients are less focused on whether or not they can detect or recognize weak (threshold) concentrations of odors. Rather, they are more concerned about the intensity at which odors are perceived. These results are consistent with the subjective responses of the patients.

In general, as noted before, ME and H values in normal subjects are similar, since subjects usually equate pleasantness or unpleasantness of any odor with its intensity, be it pleasant or unpleasant (Table V). For example, pyridine odor of 50% intensity is generally considered as 50% unpleasant whereas amyl acetate odor of 50% intensity is generally considered as 50% pleasant. Patients with hyposmia, however, may not only manifest decreased sensory acuity, but also sensory distortions. This phenomena was observed upon comparison of ME and H values between untreated patients and normals (Table II). The disparate ratios of H:ME reflected among the patients not only manifest decreased acuity (lower ME) but also the bimodal distribution of H values (as discussed previously). This bimodal distribution becomes more apparent for H values as patients recovered their sensory acuity (manifested by increased DT, RT and ME) since there was an even greater divergence of pleasantness-unpleasantness among all odors presented than in normals. Thus, H values among some patients in whom sensory acuity increased, pleasant odors (e.g., nitrobenzene—bitter almond or marzipan-like or amyl acetate—banana-like) were considered putrid because the distorted aspect of these odors also increased. This type of change may not be as readily apparent with respect to changes in more unpleasant odors (e.g., pyridine, thiophene), but may also occur with these unpleasant odors considered sweet or fruity as part of the distortion.

On 200 mg theophylline, ME values for pyridine and thiophene increased 6% and 5%, respectively, whereas H values decreased (became less unpleasant) 2%, respectively; ME values for nitrobenzene and amyl acetate increased 5%, respectively, whereas H values increased (became more pleasant) only by 2% (Table IV). This effect is better appreciated on 400 mg theophylline with ME increases for pyridine and thiophene at 12%, respectively, whereas increases in H values were 9% and 7%, respectively; ME for nitrobenzene and amyl acetate increased 11% and 8%, respectively, whereas H values decreased (became more pleasant) only 4% and 1%, respectively (Table V). Similar results hold for 600 mg theophylline also (Table VI).

Differences with respect to subjective responses and changes measured in DT and RT before and after treatment may reflect differences in how patients considered their overall improvement on treatment. A response of ≥5% was chosen to indicate improvement in smell function on treatment. This apparently small response number may in actuality be a conservative estimate of return of smell function since this number is a composite of all odors which the patient considered improved on treatment. Thus, responses to some strong odors (e.g., gasoline, bleach, ammonia, etc.) may have been considered improved by a great deal, but these responses may have been tempered by the patients' responses to weaker odors (e.g., flowers, perfume, shampoo, etc.) in which no improvement may have occurred. Therefore, the overall composite which the patient was required to consider, included overall improvement in both strong and weak odors.

Most patients are usually unconcerned whether or not they can detect or recognize weak concentrations of odors (DT or RT), but they are concerned about the intensity (ME) at which odors are perceived. After treatment with 200 mg theophylline, the average improvement in ME for all odors was 5.1% consistent with the results reported with respect to subjective responses to treatment (Table IV). After treatment with 400 mg, mean ME increased 10.4% consistent with increased response to this dose (Table V) and after treatment with 600 mg, mean ME increased 6.9% (Table VI). These results are more consistent with the subjective responses of the patients, although data for DT and RT increased significantly.

Side effects of theophylline among patients were generally minimal. Patients were required to take the drug in divided doses in middle of meals (breakfast and lunch). While this technique delayed drug absorption it did not inhibit absorption. Thus, the more common and usual side effects of nervousness, jitteriness and difficulty in falling asleep were obviated. Mild gastrointestinal upset, tachycardia, nausea, diarrhea, headache and insomnia were occasionally reported but were usually obviated by temporarily decreasing drug intake for a short period and then increasing drug dose to the required amount.

Treatment with theophylline improved smell function probably by acting through its effect as a PDE inhibitor on cAMP and cGMP levels in saliva (31) and nasal mucus (34, 35). As drug dose increased, presumably with increasing PDE inhibition, patient responses also increased. Subsequent increases in cyclic nucleotides may have increased activation of olfactory receptor stem cell growth and maturation, as previously described (20, 21).

This extensive study was performed over an extended time period in an effort to evaluate treatment of smell loss on the basis of a biochemical molecular abnormality as the basic pathology of the loss. Although unblinded, a majority of patients expressed subjective improvement in their sensory function on treatment that was confirmed through objective testing.

REFERENCES

1. Henkin, R. I. Evaluation and treatment of human olfactory dysfunction, in Otolaryngology (English, G. M. Ed.), Lippincott, Philadelphia, 1993, Vol. 2, pp. 1-86.
2. Henkin, R. I. Taste and smell disorders, human. Encyclopedia of Neuroscience, $3^{rd}$ Ed., (Adelman, G., Smith, B. H., Eds.), Birkhauser, Boston, 2004.
3. Deems, D. A., Doty, R. L., Settle, R. G., Moore-Gillon, V., Shaman, P., Mester, A. F., Kimmelman, C. P., Brightman, V. J., Snow, J. B. Jr. Smell and taste disorders, a study of 750 patients from the University of Pennsylvania Smell and Taste Center. Arch. Otolaryngol. Head Neck Surg. 1991; 177:519-528.
4. Wysocki, C. J., Gilbert, A. N. National Geographic Smell Survey: Effects of age are heterogeneous. Ann. NY Acad. Sci. 1989; 561:12-28.
5. Temmel, A. F. P., Quint, C., Schickinger-Fischer, B., Klimek, L., Stoller, E., Hummel, T. Characteristics of olfactory disorders in relation to major causes of olfactory loss. Arch. Otolaryngol. Head Neck Surg. 2002; 128:635-641.
6. Cullen, M., Leopold, D. Disorders of smell and taste. Med. Clin. North Amer. 1999; 83:57-74.
7. Bromley, S. M. Smell and taste disorders: a primary care approach. Amer. Fam. Physician. 2000; 61:427-436.
8. Seiden, A. M., Duncan, H. J., Smith, D. V. Office management of taste and smell disorders. Otolaryngol. Clin. North Amer. 1992; 25:817-835.
9. Davidson, T. M., Murphy, C., Jalowayski, A. A. Smell impairment: can it be reversed? Postgrad. Med. 1995; 98:107-109, 112-118.
10. Harris, R., Davidson, T. M., Murphy, C., Gilbert, P. E., Chem, M. Clinical evaluation and symptoms of chemosensory impairment: one thousand consecutive cases from the Nasal Dysfunction Clinic in San Diego. Amer. J. Rhinol. 2006; 20:101-108.
11. Henkin, R. I. Effects of ACTH, adrenocorticosteroids and thyroid hormone on sensory function, in Anatomical Neuroendocrinology, (Stumpf, W. E., Grant, L. D., Eds.), Karger, A. G., Basel, 1975, pp. 298-316.
12. Henkin, R. I. The role of adrenal corticosteroids in sensory processes, in Adrenal Gland, (Blaschko, H., Sayers, G., Smith, A. D., Eds.), Handbook of Physiology. Endocrinology, Washington, D.C. Amer. Physiol. Soc., Sect. 7, Vol. VI, 1975, pp. 209-230.
13. Henkin, R. I. Zinc, saliva and taste: Interrelationships of gustin, nerve growth factor, saliva and zinc, in Zinc and Copper in Clinical Medicine, (Hambidge, K. M., Nichols, B. L., Eds.), Spectrum Publ. Inc., Jamaica, N.Y., 1978, pp. 35-48.
14. Henkin, R. I., Lippoldt, R. E., Bilstad, J., Edelhoch, H. A zinc protein isolated from human parotid saliva. Proc. Nat. Acad. Sci. USA 1975; 72:488-492.
15. Henkin, R. I., Lippoldt, R. E., Bilstad, J., Wolf, R. O., Lum, C. K. L., Edelhoch, H. Fractionation of human parotid saliva. J. Biol. Chem. 1978; 253:7556-7565.
16. Henkin, R. I., Doherty, A. E., Martin, B. M. Nasal seroproteins: a new frontier in the exploration of physiology and pathology of nasal and sinus disease. New Frontiers in Immunobiology in Otolaryngology (Veldman, J. E., Passali, D., Lim, D. J., Eds.), Kugler, The Hague, 2000, pp. 127-152.
17. Henkin, R. I., Martin, B. M., Agarwal, R. P. Decreased parotid saliva gustin/carbonic anhydrase VI secretion: an enzyme disorder manifested by gustatory and olfactory dysfunction. Amer. J. Med. Sci. 1999; 318:380-391.
18. Doerty, A. E., Matin, B. M., Dai, W. L., Henkin, R. I. Carbonic anhydrase (CA) activity in nasal mucus appears to be a marker for loss of smell (hyposmia) in humans. J. Invest. Med. 1997; 45:237A.
19. Henkin, R. I., Martin, B. M., Agarwal, R. P. Efficacy of exogenous zinc in treatment of patients with carbonic anhydrase VI deficiency. Amer. J. Med. Sci. 1999; 318: 392-404.
20. Henkin, R. I., Velicu, I. Age related changes in cyclic nucleotides in saliva and nasal mucus—possible feedback mechanism in development of gustatory and olfactory receptor function. FASEB J. 2005; 19:A1368.
21. Papathanassiu, A., Henkin, R. I. cAMP is present in human nasal mucus and may act as a growth factor in cells of the olfactory epithelium. FASEB J. 2002; 16:A1153.
22. Asakura, K., Kataura, A. cAMP and cGMP in the human parotid saliva. Arch. Otorhinolaryngol. 1980; 226:1529-30.
23. Schaeffer, L. D., Sproles, A., Krakowski, A. Detection of cAMP in parotid saliva of normal individuals. J. Dent. Res. 1973; 52:629.
24. Glenert, U., Geisler, A. A single assay for cyclic adenosine 3':5'-monophosphate in human saliva. J. Cyclic Nucleotide Protein Phosphor. Res. 1985; 10:451-461.
25. Hanamori, T., Nagotsu, T., Matsumoto, S. Origin of cyclic adenosine monophosphate in saliva. J. Dent. Res. 1975; 54:535-539.
26. Rosenzweig, S., Yan, W., Sasso, M., et al. Possible novel mechanism for bitter taste mediated through cGMP. J. Neurophysiol. 1999; 81:1661-5.
27. Pace, U., Hanski, E., Salomon, Y, et al. Odorant-sensitive adenylate cyclase may mediate olfactory reception. Nature. 1985; 316:255-8.
28. Anholt, R. R. H. Molecular neurobiology of olfaction. Crit. Rev. Neurobiol. 1993; 7:1-22.
29. Firestein, S., Zufall, F., Sheperd, G. M. Single odorsensitive channels in olfactory receptor neurons are also gated by cyclic nucleotides. J. Neurosci. 1991; 11:3565-72.
30. Moon, C., Simpson, P. J., Cho, H., et al. Regulation of intracellular cyclic GMP levels in olfactory sensory neurons. J. Neurochem. 2005; 95:200-9.
31. Henkin R. I., Velicu I., Papathanasiu A. cAMP and cGMP in human parotid saliva: relationships to taste and smell dysfunction, gender and age. Amer. J. Med. Sci. 2007; 334:431-440.
32. Henkin, R. I., Velicu, I. cAMP and cGMP in nasal mucus: relationships to taste and smell dysfunction, gender and age. Clinical Invest. Med. 2008; 31:E71-E77.
33. Henkin, R. I. The definition of primary and accessory areas of olfaction as the basis for a classification of decreased olfactory acuity, in Olfaction and Taste II, (Hayashi, T. Ed.), Pergamon Press, London, 1967, pp. 235-252.
34. Henkin, R. I., Velicu, I. Decreased parotid salivary cyclic nucleotides related to smell loss severity in patients with taste and smell dysfunction. Metabolism. 2009; in press.

35. Henkin, R. I., Velicu, I. cAMP and cGMP in nasal mucus related to severity of smell loss in patients with smell dysfunction. Clinical Invest. Med. 2008; 31:E78-E84.
36. Cai, D., Qiu, J., Cao, Z., McAtee, M., Bregman, B. S., Filben, M. T. Neuronal cyclic AMP controls the developmental loss in ability of axons to regenerate. J. Neurosci. 2001; 21:4731-4739.
37. Neumann, S., Bradke, F., Tessier-Lavigne, M., Basbaum, A. I. Regeneration of sensory axons within the injured spinal cord induced by intraganglionic cAMP elevation. Neuron. 2002; 34:885-893.
38. Cai, D., Shen, Y., DeBellard, M., Tang, S., Filben, M. T. Prior exposure to neurotrophins blocks inhibition of axonal regeneration by MAG and myelin via a cAMP dependent mechanism. Neuron. 1999; 22:89-101.
39. Kurihara, K., Koyama, N. High activity of adenylyl cyclase in olfactory and gustatory organs. Biochem. Biophys. Rev. Comm. 1972; 48:30-34.
40. Pace, U., Hanski, E., Salomon, Y., Lancet, D. Odorant-sensitive adenylate cyclase may mediate olfactory reception. Nature. 1985; 316:255-258.
41. Moon, C., Simpson, P. J., Cho, H., Ronnett, G. Y. Regulation of intracellular cyclic GMP levels in olfactory sensory neurons. J. Neurochem. 2005; 95:205-209.
42. Shepherd, G. M. Sensory transduction entering the mainstream of membrane signaling. Cell. 1991; 67:845-851.
43. Thompson, W. J. Cyclic nucleotide phosphodiesterase: pharmacology, biochemistry and function. Pharmacol. Ther. 1991; 51:13-33.
44. Firestein, B. I., Bredt, D. S. Regulation of sensory neuron precursor proliferation by cyclic GMP-dependent protein kinase. J. Neurochem. 1998; 71:1846-1853.
45. Anholt, R. R. H. Molecular neurobiology of olfaction. Crit. Rev. Neurobiol. 1993; 7:1-22.
46. Henkin, R. I., Velicu, I., Papathanasiu, A. Dichotomous changes in cAMP and cGMP in human parotid saliva after oral theophylline. FASEB J. 2003; 17:A1028.
47. Velicu, I., Henkin, R. I. On the antiapoptotic mechanism of action of theophylline in restoring smell function in patients with hyposmia. J. Invest. Med. 2005; 53(Suppl. 2):S402.
48. Levy, L. M., Henkin, R. I., Hutter, A, Lin, C. S., Schellinger, D. Increased brain activation in response to odors in patients with hyposmia after theophylline treatment demonstrated by fMRI. J. Comp. Asst. Tomog. 1998; 22:760-770.
49. Henkin, R. I., Velicu, I., Schmidt, L. Effective treatment of smell loss with theophylline. Exper. Biol. 2008; 22:B976.2.
50. Henkin, R. I., Larson, A. L., Powell R. D. Hypogeusia, dysgeusia, hyposmia and dysosmia following influenza-like infection. Ann. Otol. Rhin. Laryngol. 1975; 84:672-682.
51. Church, J. A., Bauer, H., Bellanti, J. A., Satterly, R. A., Henkin, R. I. Hyposmia associated with atopy. Ann. Aller. 1978; 40:105-109.
52. Schechter, P. J., Henkin, R. I. Abnormalities of taste and smell following head trauma. J. Neurol. Neurosurg. Psychiat. 1974; 37:802-810.
53. Henkin, R. I., Schecter, P. J., Friedewald, W. T., DeMets, D. L., Raff, M. S. A double blind study of the effects of zinc sulfate on taste and smell dysfunction. Amer. J. Med. Sci. 1976; 272: 285-299.
54. Henkin, R. I., Schechter, P. J., Hoye, R. C., Mattern, C. F. T. Idiopathic hypogeusia with dysgeusia, hyposmia and dysosmia: a new syndrome. J. Amer. Med. Assoc. 1971; 217:434-440.
55. Schechter, P. J., Friedwald, W. T., Bronzert, D. A., Raff, M. S., Henkin, R. I. Idiopathic hypogeusia: a description of the syndrome and a single blind study with zinc sulfate, in Internat. Rev. Neurobiol. Suppl. 1., (Pfeiffer, C., Ed.), Academic Press, NY, 1972, pp. 125-133.
56. Henkin, R. I. The definition of primary and accessory areas of olfaction as the basis for a classification of decreased olfactory acuity, in Olfaction and Taste II, (Hayashi, T. Ed.), Pergamon Press, London, 1967, pp. 235-252.

Example 2

Theophylline treatment restored smell function in over 50% of the hyposmic patients in Example 1. This study, however, was an open label clinical trial and not all patients responded to the drug. These results raise questions about the character of the study and the efficacy of the drug to correct the smell loss.

In an effort to understand more about these results, levels of cAMP and cGMP in saliva before and after theophylline treatment were studied in patients who participated in the clinical study of Example 1. Cyclic nucleotide levels were not assayed until the entire analysis of the clinical trial results was completed.

Methods

Thirty-one patients, aged 29-85 y (56±3 y, Mean±SEM) from among the 312 patients who participated in the open label, fixed design clinical trial treated with theophylline of Example 1 were studied. There were 13 men, aged 54±3 y and 18 women, aged 58±4 y. All patients exhibited hyposmia. Six had Type I hyposmia, 25 had Type II hyposmia. Patients had a variety of etiologies for their hyposmia; six had PVIL and hypogeusia, thirteen had allergic rhinitis, nine had a head injury, and three had a variety of the etiologies contributing to their loss including a drug reaction, an idiopathic cause and post chemotherapy.

Measurements of smell function were obtained for each patient by use of a standard three stimuli forced choice technique using four odors (pyridine, nitrobenzene, thiophene and amyl acetate as described in Example 1. Subjective measurements of smell function were also obtained for each patient by use of standard technique in which smell acuity was graded on a scale from 0-100 with 0 indicating an absence of overall smell function and 100 indicating normal smell function as described in Example 1.

Parotid saliva was collected from each patient by application of a Lashley cup over Stensen's duct with lingual stimulation by placement of concentrated lemon juice. Saliva was collected in plastic tubes and stored at −20° C. until assayed. cAMP and cGMP were measured in saliva by a sensitive 96 plate spectrophotometric assay (R&D Systems, Minneapolis, Minn.).

All patients were placed in a fixed design open label clinical trial with treatment with oral theophylline. Treatment consisted of fixed treatment periods of two-eight months with sequential doses of the drug at 200 mg, 400 mg and 600 mg. At termination of each of these intervals, patients returned to study site for reevaluation. At the end of each interval subjective responses to treatment were measured with a modification of the 0-100 scale previously used (vs). Subjective responses to treatment were graded on a sliding scale from −100-0∓100 with patients recording improvement (+0∓100), no improvement (0) or worsening (0−−100) of their overall smell function. If overall smell function improved >5% they were considered to improve clinically (1). If smell function improved <5% they were considered not to improve (1). At the end of each interval subjective measurements of smell function, measurements of DT, RT, ME and H and measurements of parotid saliva for levels of cAMP and cGMP were obtained. In addition, blood plasma was obtained by venipuncture, placed in ice into zinc free tubes which contained 100 mg zinc free heparin, centrifuged at 3000 rpm for 10-20 min, the plasma transferred to plastic PCR tubes and stored at −20° C. until assayed. Theophylline was assayed by a fluorescence polarization assay (Abbott, Chicago, Ill.), as previously described.

At each return visit, if patients noted improvement in their overall smell function (see Example 1) they continued on this same drug dose and were not included in any further data. If smell function did not improve on 200 mg of theophylline, their dose was increased to 400 mg and they returned to study site after an additional two-four months of treatment. These same measurement processes occurred after treatment with 400 mg and 600 mg of theophylline.

Data for the cyclic nucleotides from these 31 patients was not analyzed until the entire study of the 312 patients in Example 1 was assembled and analyzed in its entirety. After completion of these analyses, all data for parotid saliva cAMP and cGMP from all patients in whom salivary cAMP and cGMP were obtained were assembled. Levels of salivary cyclic nucleotides varied widely. Initially, without external criteria, there was no way to understand these disparate data. To assist in understanding these data, each data point was independently identified with respect to which patient from whom it was obtained and categorized as to whether or not that patient demonstrated improvement or lack of improvement in both subjective smell function and in objective measurements of smell function (DT, RT, ME, H) on theophylline treatment. On this basis, 20 patients were identified as having improved smell function and 11 did not improve. In a similar manner, measurements of each patient's plasma theophylline level at each dosage of theophylline (at 200 mg, 400 mg, 600 mg of theophylline) were catagorized. The two patient groups were also analyzed post hoc with respect to type of smell loss and etiology of smell loss.

Differences in the characteristics between these two patient groups were analyzed with respect to each measurement obtained (Mean±SEM). Differences between mean±SEM were analyzed using Student t test and X2; differences of $p \leq 5\%$ were considered significant.

Results

Post hoc analysis demonstrated that initial values of subjective smell function and measurements of smell function (DT, RT, ME, H) from these two patient groups prior to theophylline treatment did not differ. At baseline, there were also no significant differences in saliva cAMP and cGMP between improved and unimproved patients (Table XI). Levels of saliva cAMP prior to treatment were consistent with mean values obtained for saliva cAMP in all 312 patients included in the original study. After treatment with 200 mg of theophylline, cAMP levels in the improved patients increased 10% above baseline, albeit not significantly; there was essentially no change among the unimproved patients (Table I). After treatment with 400 mg of theophylline, however, although values were not statistically significant compared to before treatment, cAMP levels increased 40% over baseline in the improved group, whereas there was essentially no change among the unimproved patients. After treatment with 600 mg, cAMP levels increased significantly to 67% above initial cAMP values in the improved patients, but there was essentially no change among unimproved patients. After treatment with 600 mg, levels of cAMP in the improved patients were still below the mean of saliva cAMP reported in normal subjects.

TABLE XI

RESULTS FOR PATIENTS WITH IMPROVED SMELL FUNCTION

| BEFORE TREATMENT | THEOPHYLLINE TREATMENT cAMP (pmol/ml) | | | BEFORE TREATMENT | THEOPHYLLINE TREATMENT cGMP (pmol/ml) | | | PLASMA THEOPHYLLINE | | |
|---|---|---|---|---|---|---|---|---|---|---|
| (pmol/ml) | 200 mg | 400 mg | 600 mg | (pmol/ml) | 200 mg | 400 mg | 600 mg | (mg/dl) | | |
| 0.87 ± 0.14* (20) | 0.96 ± 0.13 (16) | 1.22 ± 0.33 (12) | $1.45^b$ ± 0.37 (9) | 0.08 ± 0.016 (20) | 0.08 ± 0.016 (15) | $0.22^a$ ± 0.07 (12) | $0.27^a$ ± 0.09 (10) | 3.5 ± 0.4 (13) | 6.4 ± 1.2 (12) | $12.4^a$ ± 1.8 (9) |

*Mean ± SEM
( ) Patient number
With respect to no improvement in smell function
$^a p < 0.05$
$^b p < 0.025$ At baseline, there were no significant differences between cGMP levels for the two groups of patients (Table XII). Mean values obtained in each patient group were consistent with values obtained in the total group of 312 patients prior to initiation of the treatment (see Example 1). After treatment with 200 mg of theophylline, there was little difference in saliva cGMP levels between improved and unimproved patients or compared to pretreatment values. After treatment with 400 mg of theophylline, saliva cGMP levels in the improved patients increased significantly to 275% over initial values, whereas there was little change among the unimproved patients. After treatment with 600 mg of theophylline, cGMP levels improved significantly to 338% over initial values, whereas there was no increase among the unimproved patients. After treatment with 400 mg or 600 mg of theophylline, cGMP mean levels in the improved patients were similar to those obtained in normal subjects.

TABLE XII

RESULTS FOR PATIENTS WITH UNIMPROVED SMELL FUNCTION

| BEFORE TREATMENT | THEOPHYLLINE TREATMENT cAMP (pmol/ml) | | | BEFORE TREATMENT | THEOPHYLLINE TREATMENT cGMP (pmol/ml) | | | PLASMA THEOPHYLLINE (mg/dl) | | |
|---|---|---|---|---|---|---|---|---|---|---|
| (pmol/ml) | 200 mg | 400 mg | 600 mg | (pmol/ml) | 200 mg | 400 mg | 600 mg | 200 mg | 400 mg | 600 mg |
| 1.03 ± 0.24* (11) | 0.78 ± 0.26 (9) | 0.95 ± 0.26 (5) | 0.56 ± 0.21 (9) | 0.08 ± 0.016 (11) | 0.07 ± 0.018 (9) | 0.05 ± 0.014 (4) | 0.04 ± 0.07 (5) | 3.7 ± 1.0 (9) | 8.6 ± 1.4 (5) | 8.7 ± 0.6 (9) |

*Mean ± SEM
( ) Patient number

Comparison of blood plasma theophylline between the two groups indicated that there was no difference in mean values after treatment with either 200 mg or 400 mg of theophylline (Table XI). After treatment with 600 mg, however, although plasma theophylline increased in both groups, compared to plasma levels seen following treatment with 200 mg or 400 mg of theophylline, mean theophylline was significantly elevated in the improved group compared to the unimproved group. (Tables XI and XII).

Classified by smell loss type, there were significant differences between the two groups (Table XIII). Among the improved patients, 95% of the patients exhibited Type II hyposmia, whereas, only one patient had Type I hyposmia. Among the unimproved patients, 57% of the patients exhibited Type I hyposmia, indicating that significantly more of the unimproved patients (with unchanged levels of cAMP and cGMP) had Type I hyposmia, the more severe type of smell loss (Table XII).

TABLE XIII

COMPARISON OF CLINICAL CHARACTERISTICS BETWEEN IMPROVED AND UNIMPROVED PATIENTS

| | IMPROVED * | | UNIMPROVED | |
|---|---|---|---|---|
| SMELL LOSS TYPE | I | II | I | II |
| PATIENT NUMBER | 1 | 19[a] | 4 | 7 |

| | IMPROVED* | | | | UNIMPROVED | | | |
|---|---|---|---|---|---|---|---|---|
| | AR | PIHH | HI | OTHER | AR | PIHH | HI | OTHER |
| ETIOLOGY OF LOSS | | | | | | | | |
| PATIENT NUMBER | 8 | 6 | 3 | 3 | 8 | 0 | 3 | 0 |

*Parotid saliva cAMP and cGMP concentrations after 600 mg theophylline were significantly higher in improved than in unimproved patients (see Tables I, II)
Improved vs Unimproved by Smell Loss Type
[a]$X^2 = 5.2$ (p < 0.05)
AR, allergic rhinitis
PIHH, post influenza-like hyposmia and hypogeusia
HI, head injury
Other (drug reaction, idiopathic, post chemotherapy)

Classified by diagnosis, the distribution of etiology of smell loss among the improved patients was similar to that previously reported in several publications. Among the unimproved patients, however, there were no patients who had PIHH or "other" causes of smell loss. Indeed, only two etiologies comprised the etiology of smell loss among unimproved patients, either allergic rhinitis or head injury (Table XII).

Discussion

The observed results were unexpected. These results, however, suggest that changes in cGMP may be more relevant to changes in smell function than measurement of cAMP since, among the improved patients, levels of cGMP increased into the normal range whereas for cAMP they increased, but not into the normal range.

These results also suggest that administration of theophylline at the same dose results in differences in smell improvement, in levels of saliva cAMP or cGMP and in serum theophylline levels in this group of patients. There are no prior studies that would suggest differential effects of drug response or biochemical changes related to theophylline intake. This type of change, however, has been observed previously with many drugs and is well known in several disease states. Indeed, drug resistance has been important to understanding differential drug affects and their influence on metabolic processes. Although the patient number in this study is relatively small, apparently this is the first report of drug resistance to oral administration of theophylline.

Patients with theophylline resistance appear to have specific clinical characteristics by which they can be identified prior to their treatment and development of this resistance. It was discovered that unimproved patients had head injury and allergic rhinitis. In addition these patients exhibit a preponderance of a severe type of smell loss (Type I hyposmia), one in which they cannot recognize the character of any odor.

The data obtained also suggest that this resistance is present irrespective of drug dose, although it is more obvious at higher doses of the drug. In addition, drug resistance effects appear to be more robust with respect to levels of saliva cGMP rather than to cAMP. Levels of salivary cGMP among the improved patients returned to levels previously observed in normal subjects. Saliva cAMP levels increased, significantly so at the highest dose of theophylline administered, but they did not increase to levels measured in normal subjects.

While levels of blood theophylline increased in both groups of patients as the dose of theophylline increased (200 mg, 400 mg, 600 mg), levels of blood theophylline were significantly higher in the improved group compared to the unimproved group after 600 mg of the drug. The blood theophylline level in the improved group was 12.4 mg/dl whereas it was 8.7 mg in the unimproved group (Tables XI and XII). While the level of theophylline in the improved patients is in the normal range for therapeutic effects of the drug (10-20 mg/dl), the level in the unimproved group was not. Previous data suggest that patients that improve with theophylline exhibit plasma levels between 2-14 mg/dl, so that it would not be reasonable to imply that these differences between these two groups are attributable only to the differences obtained in serum theophylline. While this is undoubtedly one factor related to drug resistance, as is well known from many other studies, this difference may not account for all the differences between these two groups.

The open label trial of theophylline in Example 1 demonstrates the usefulness of theophylline in restoring the sense of smell in patients with smell loss. The present studies indicate that multiple factors influence successful treatment of hyposmic patients and that a thorough work up is required if treatment is to be successful. These factors include testing as to the type and degree of smell loss, discovering the etiology of the patient's smell loss, analysis of theophylline plasma levels, and analysis of parotid gland secretion of cAMP and cGMP. In particular, parotid saliva cGMP level stands out as predictive of clinical response given the unexpected finding that cGMP levels correlate with recovery of the sense of smell. This observation allows for the development of a testing regiment to select for the appropriate therapy. A patient can be administered a standard challenge dose of theophylline or other PDE inhibitor and then the level of parotid saliva cGMP is determined. Patients that achieve a threshold level of cGMP following the challenge can then be prescribed the appropriate dose that will achieve the targeted steady state plasma level of the PDE inhibitor. Patients whom parotid saliva cGMP levels fail to achieve the threshold level can be challenged with a higher dose of the PDE inhibitor, have another PDE inhibitor or other active agent added to the dosage of the original PDE inhibitor, or switched to another PDE inhibitor as is clinically warranted. In this way, a physician can determine the optimum PDE inhibitor dosage for a patient without undertaking the long dose escalation titration required in the original study detailed in Example 1.

In some embodiments, a method is provided for screening patients for PDE inhibitor therapy for anosmia or hyposmia comprising: administering to a patient a challenge dose of a PDE inhibitor; determining the salivary level of cGMP; and comparing the patient's salivary cGMP level to a threshold value, wherein patients who have a cGMP salivary level equal to or greater than the threshold value are candidates for PDE inhibitor therapy to treat anosmia or hyposmia. In some embodiments, the challenge dose is 200 mg, 400 mg, 600 mg or 800 mg of theophylline. In some embodiments, the threshold value is at least 0.08, 0.10, 0.12, 0.14, 0.16, 0.18, 0.20, 0.22, 0.24, 0.26, or 0.28 pmol/ml.

In some embodiments, the threshold value is equal to or substantially similar to the mean cGMP value seen in normal individuals following the same challenge dose. In other embodiments, the threshold value is not less than 10%, 20%, 30%, 40%, or 50% of the mean salivary cGMP value seen in normal individuals following the same challenge dose.

Example 3

Hyposmic patients for whom the etiology of smell loss is not associated with head injury or allergic rhinitis are enrolled in an open label trial of inhalable theophylline. Patients are started at an initial dose of not more than 500 μg formulated as a liquid spray or dry powder to be delivered as a metered dose. Initially only local patients are enrolled so that quicker dose titration is achieved. Groups of 5 patients are started on not more than 500 μg of theophylline and continued for 1 month.

Patients are tested for improvement in smell acuity using the standard forced choice technique using four odors as described in Example 1. Additionally, subjective measurements of smell function are obtained using a scale from 0-100 as described in Example 1. Blood samples are also drawn to ascertain blood theophylline level to gauge its relationship to the expected recovery of smell.

Nasal administration of theophylline provides for high, initial concentrations of theophylline being deposited on the olfactory epithelium, thereby exposing olfactory neurons and their sensory cilia to higher concentrations of theophylline than are achieved through oral administration through the avoidance of first pass metabolism. Nasal administration provides for at least an equivalent recovery of smell acuity comparable to that achieved with orally administered theophylline while avoiding or at least reducing the side effects caused by higher theophylline plasma levels seen with oral administration.

Example 4

Hyposmic patients for whom the etiology of smell loss is not associated with head injury or allergic rhinitis are enrolled in an open label trial of an inhalable PDE1 inhibitor. More preferably, a PDE1C2 inhibitor such as ebumamenine-14-carboxylic acid ethyl ester (vinpocetine), 8-methoxymethyl-1-methyl-3-(2-methylpropyl) xanthine (8MM-IBMX), zaprinast (M&B 22948), 4-[3-(cyclopentyloxy)-4-methoxyphenyl]-2-pyrrolidinone (rolipram), 4-(3-butoxy-4-methoxybenzyl)-2-imidazolidinone (RO20-1724), 1,6-dihydro-2-methyl-6-oxo-(3,4'-bipyridine)-5-carbonitrile (milrinone), trequinsin (HL 725), and/or combinations thereof because of the high expression level of PDE1C2 in the olfactory epithelium. Patients are started at an initial dose of 500 μg formulated as a liquid spray or dry powder delivered as a metered dose. Initially only local patients are enrolled so that quicker dose titration is achieved. Groups of 5 patients are started on 500 μg of the PDE1 inhibitor or PDE1C2 inhibitor and continued for 1 month.

Patients are tested for improvement in smell acuity using the standard forced choice technique using four odors as described in Example 1. Additionally, subjective measurements of smell function are obtained using a scale from 0-100 as described in Example 1. Blood samples are also drawn to ascertain blood levels of the PDE1 inhibitor or PDE1C2 inhibitor and its relationship to the observed patient response.

Nasal administration of the PDE1 inhibitor or PDE1C2 inhibitor provides higher exposure of the PDE1 inhibitor or PDE1C2 inhibitor to nasal olfactory neurons than can be achieved through oral administration. This provides for at least an equivalent recovery of smell acuity comparable to that achieved with orally administered PDE 1 inhibitor or PDE1 C2 inhibitor, avoiding or reducing the side effects caused by higher PDE1 inhibitor or PDE1C2 inhibitor plasma levels seen with oral administration.

Example 5

For over 60 years, theophylline has been used as a bronchodilator in the treatment of asthma and COPD and remains one of the most widely prescribed drugs for the treatment of airway diseases worldwide. Theophylline directly relaxes human airways smooth muscle in vitro and, like $beta_2$-agonists, acts as a functional antagonist, preventing and reversing the effects of all bronchoconstrictor agonists. Bronchodilatation by theophylline is achieved through PDE inhibition, resulting in an increase in cAMP by inhibition of PDE3 and PDE4 and in cyclic guanosine 3',5'-monophosphate by inhibition of PDE5. The bronchodilator effect of theophylline in human airways is reduced by charybdotoxin, which selectively inhibits large conductance $Ca^{2+}$ activated $K^+$ channels (maxi-K channels), suggesting that theophylline opens these maxi-K channels via an increase in cAMP.

In asthma therapy, theophylline has an increasing acute bronchodilator response above plasma concentrations of 10 mg/L (55 μM), however, the upper recommended plasma concentration is 20 mg/L due to unacceptable side effects above this level including nausea and headaches. The therapeutic range for plasma concentrations is therefore established at 10 to 20 mg/L, and doses are adjusted in individual patients to achieve this range.

Theophylline has an additional effect on mucociliary clearance through a stimulatory effect on ciliary beat frequency and water transport across the airway epithelium. Relatively high doses of theophylline are needed, as this effect is likely to be due to an increase in cAMP as a result of PDE inhibition.

Theophylline also has anti-inflammatory effects in asthma. In allergen challenge studies in patients with asthma, intravenous theophylline inhibits the late response to allergen. A similar finding with allergen challenge was reported after chronic oral treatment with theophylline. Oral theophylline also inhibits the late response to toluene diisocyanate in toluene diisocyanate-sensitive individuals with asthma. This is interpreted as an effect on the chronic inflammatory response, and this is supported by a reduced infiltration of eosinophils and $CD4^+$ lymphocytes into the airways after allergen challenge subsequent to low doses of theophylline. In patients with nocturnal asthma, low-dose theophylline inhibits the influx of neutrophils and, to a lesser extent, eosinophils in the early morning. In patients with mild asthma, low doses of theophylline (mean plasma concentration ~5 mg/L) reduce the numbers of eosinophils in bronchial biopsies, bronchoalveolar lavage, and induced sputum, whereas in severe asthma, withdrawal of theophylline results in increased numbers of activated $CD4^+$ cells and eosinophils in bronchial biopsies.

In patients with COPD, theophylline reduces the total number and proportion of neutrophils in induced sputum, the concentration of interleukin-8, and neutrophil chemotactic responses, suggesting an antiinflammatory effect. This is in sharp contrast to the lack of effect of high doses of inhaled corticosteroids in a similar population of patients.

These anti-inflammatory effects of theophylline in asthma and COPD are seen at concentrations that are usually less than 10 mg/L, which is below the dose where significant clinically useful bronchodilatation is evident.

Theophylline is a weak and nonselective inhibitor of PDEs. In vitro, theophylline relaxes airway smooth muscle by inhibition of PDE activity (PDE3, PDE4, and PDES), but relatively high concentrations are needed for maximal relaxation. The degree of PDE inhibition is very small at concentrations of theophylline that are therapeutically relevant with experiments with human lung extracts demonstrating only 5 to 10% inhibition of total PDE activity at therapeutic concentrations.

Inhalation therapy with neublized solutions of theophylline and other methylxanthines was tried to widen the therapeutic index. Inhalation of methylxanthine derivatives produce an immediate increase in specific airway resistance (sGaw) that peaks in 5 minutes, but the effects were no more than half the response seen with a standard 200 μg dose of inhaled salbutamol, and dissipated by 30 minutes. Additionally, the nebulized solutions of methylxanthine derivatives have a disagreeable taste and produced a pronounced cough leading the researchers to conclude that inhalation of methylxanthines derivatives were unlikely to be of benefit in the treatment of asthma.

Applicants believe that this past failure with inhalable methylxanthine derivatives owes more to the formulation and method of delivery than to the inherent properties of the derivatives. To test this theory, asthmatic patients are enrolled in a dose escalating single blind study. On arrival to the clinic, subjects are allowed to rest for 20 minutes before baseline measurements of FEV1 (six recordings) and sGaw (five recordings) are made. Subjects receive a dry powder dispenser loaded with a dose of 2 mg theophylline or a dry powder carrier. Subjects are advised that some of the preparations may have a bitter taste, while others will not, but that this does not necessarily reflect the presence or degree of activity of the drug. After each inhalation, measurements of sGaw are made at 1, 3, 5, 10, 15, 20, 25, and 30 minutes. After 30 minutes, the sGaw measurement is still 20% above the baseline measurement, so additional sGaw measurements are taken every 15 minutes until baseline is reached at 1 hour.

On completion of the last recording, subjects inhale a 200 μg dose of salbutamol from a metered inhaler and a further measurement of sGaw is made after 15 minutes. Subjects are also monitored for coughing and are questioned about the taste of the drug. The increase in sGaw produced by the inhaled theophylline is comparable to that produced by salbutamol. Furthermore, the dry powder formulation is without the unpleasant taste or the induction of coughing associated with a liquid formulation delivered by a nebulizer.

Example 6

IBMX, (isobutylmethylxanthine), a non-specific PDE inhibitor possesses greater potency than theophylline (IC50=2-50 μM). Given IBMX structural similarity to theophylline, IBMX shares theophylline's bronchodialation, anti-inflammatory, and ciliary beat frequency stimulatory effects but is expected to have a wider therapeutic index potentially allowing for the use of lower dosages, thereby reducing side effects and complaints over disagreeable taste when administered through a nebulizer.

Asthmatic patients are enrolled in a dose escalating single blind study. On arrival to the clinic, subjects are allowed to rest for 20 minutes before baseline measurements of FEV1 (six recordings) and sGaw (five recordings) are made. Subjects receive a dry powder dispenser loaded with a dose of 1 mg IBMX formulated as a dry powder or a dry powder carrier. Subjects are advised that some of the preparations may have a bitter taste, while others will not, but that this does not necessarily reflect the presence or degree of activity of the drug. After each inhalation, measurements of sGaw are made at 1, 3, 5, 10, 15, 20, 25, and 30 minutes. After 30 minutes, the sGaw measurement is still 20% above the baseline measurement, so additional sGaw measurements are taken every 15 minutes until baseline is reached at one and a half hours.

On completion of the last recording, subjects inhale a 200 μg dose of salbutamol from a metered inhaler and a further measurement of sGaw mad after 15 minutes. Subjects are also be monitored for coughing and are questioned about the taste of the drug. The increase in sGaw produced by the inhaled IBMX is comparable with that produced by salbutamol. Furthermore, the dry powder formulation is without the unpleasant taste or the induction of coughing associated with a liquid formulation delivered by a nebulizer.

Example 7

Ten patients with hyposmia were selected from among 400 patients with hyposmia to participate in a pilot study to determine safety and efficacy of intranasal theophylline for the treatment of hyposmia. These patients were previously treated with oral theophylline or were switched from oral theophylline to intranasal theophylline at the start of the study. Selection for inclusion in the intranasal study was based upon several criteria. 1) non-response to oral theophylline; 2) severe side effects with oral theophylline that prevented reaching a dose of sufficient strength to restore smell function; and/or 3) preference for intranasal medication over oral medication.

Through careful evaluation of plasma, saliva and nasal mucus theophylline levels in patients with hyposmia taking theophylline at doses of 200-800 mg daily, it was determined that a dose of 20 μg theophylline delivered intranasally to each naris (or 40 μg total) was sufficient to produce localized effects similar to those achieve with oral theophylline of 200-400 mg daily. Additionally, loco-regional administration of such a low dose would avoid producing the side effects seen with oral administration.

Intranasal Preparation

A batch of theophylline for intranasal administration at a dose of 20 μg/0.4 ml of was prepared by dissolving 250 mg of methylparaben powder and 250 mg of propylparaben powder in 5 ml of propylene glycol. Next 50 mg of theophylline, anhydrous powder, was dissolved in a small amount of 0.9% sodium chloride. The dissolved parabens were added to the theophylline solution and mixed well. Sufficient 0.9% sodium chloride was added to the mixture to bring the total volume to 1000 ml. The solution was sterilized by filtering through a sterile 0.2 μm filter. 1 ml syringes were loaded with 0.4 ml of the sterile solution and then capped with a tamper evident cap. Representative samples were sent to an independent testing laboratory for pH, endotoxin, sterility, and fungal contamination testing in addition to the determination of the theophylline concentration. The test results demonstrated that the preparation had 20.716 μg of theophylline per 0.4 ml with a pH of 5.9. Further, endotoxin was below 1.0 EU/ml and the preparation was sterile and free of fungal contamination.

Study Design

The purpose, risk and benefits of participating in the study were explained to each patient by the study's supervising physician. Prior to enrollment in the study, each patient read and signed an informed consent form. Next, each patient was instructed in the proper technique of intranasal administration.

Patients discontinued their use of oral theophylline either at time of entry into the study (eight patients) or four months prior to study entry (two patients).

Changes to smell function was determined at four specific periods:

Time 0—at the start of the study.
Time 1—one week after starting intranasal theophylline
Time 2—two weeks after starting intranasal theophylline
Time 4—four weeks after starting intranasal theophylline After reaching Time 4, the study was discontinued and the patients were returned to their use of oral theophylline if indicated.

Study Measurements

At each of the four time periods of the study the following battery of tests were performed and samples obtained.

Objective Test Measurements

Taste Function Tests

Taste function was measured by detection threshold (DT), recognition threshold (RT), magnitude estimation (ME) and hedonics (H) for four tastants (NaCl, sucrose, HCl, urea) by use of a standard three stimuli, forced choice staircase drop technique described in Example 1 and ref 53.

Smell Function Tests

Smell function was measured for DT, RT, ME and H for four odorants (pyridine, nitrobenzene, thiophene, amyl acetate) by use of the standard three stimuli, forced choice staircase sniff technique described in Example 1 and in ref 53.

Bodily Fluids

Blood was obtained by venipuncture to collect plasma and red blood cells used to measure trace metals (Cu, Zn, Mg), various enzymes, theophylline and other chemical moieties.

Saliva was collected with a modified Lashley cup as described in Example 2 and used to measure trace metals (Cu, Zn, Mg), various enzymes (cAMP, cGMP, CA VI, etc.), theophylline and other chemical moieties.

Nasal mucus was collected by use of a standard technique and used to measure trace metals (Cu, Zn, Mg), various enzymes (cAMP, cGMP, CA VI, etc.), theophylline and other chemical moieties. Trace metals were measured by atomic absorption spectrophotometry (as previously decscribed) using a dual beam Thermo-Jarrel Ash atomic absorption spectrophotometer. CA VI was measured by enzymatic analysis of activity of the enzyme by our modification of the method of Richli, et al. Cyclic nucleotides were measured by a sensitive 96 plate spectrophotometric sensitive ELISA assay provided by Applied Biosystems, Minneapolis, Minn.

Subjective Test Measurements

Subjective responses to treatment were obtained independent of any interaction with the clinical staff by using a scale of 0-100 to measure response of taste function and smell function to treatment with 0 indicating no response, 100 indicating return to normal function and intermediate numbers indicating an intermediate response.

Treatment Technique

The patients inserted a plastic syringe containing 0.4 ml of fluid (20 μg theophylline) into each naris once a day. Previous investigation of the syringe injection technique for intranasal drug administration indicated that a volume of 0.4 ml delivered to each naris was sufficient to deliver the drug dose without having the liquid escape out of the nares or directly into the pharynx. The drug dose was delivered through a plastic nipple which fitted snugly onto the filled syringe which was attached directly to the nipple. One nipple was supplied for each set of two syringes in each application kit. The patient fitted the nipple on one syringe, placed the nipple securely into the lower naris and injected the contents of the syringe directly into the lower vault of one naris accompanied by a modest inhalation. This technique was then used for the second syringe used for the other naris. The patients were instructed to administer the drug either seated or standing with their head in an erect, vertical position.

Patients were supplied with 15 doses on each of two occasions with all used syringes returned to the clinic after use to insure proper and complete usage.

Results

Ten hyposmia patients were enrolled in the study, eight patients have completed all four phases of the study with the remaining two patients still in process. No side effects of intranasal use were observed, including, no nasal congestion, nasal pruritus, nasal discomfort, cough or unusual or bitter taste. No patient exhibited a further of loss of smell while in the study. This demonstrates that the patients that stopped their oral medication at the time of the start of the study, which ranged from 400-800 mg oral theophylline daily, received at least an equivalent localized dose of theophylline to the nasal olfactory epithelium as was achieved with their total oral dose.

Of the eight patients that completed the study, six reported subjective improvement in both taste and smell function (>10-20% over prior results with oral theophylline). The plasma theophylline levels for the eight patients was zero indicating that at most an undetectable fraction of intranasal theophylline was absorbed systemically. Furthermore, this data demonstrates that at the dosage level of 20 μg per naris, more theophylline is delivered locally to the nasal olfactory epithelium than is delivered by 200-800 mg of oral theophylline because the six patients that experienced increased smell acuity with the intranasal theophylline reported that their acuity diminished upon the resumption of their previous oral dosage of theophylline.

Overall, of the first eight patients, six (75%) exhibited subjective improvement in smell function in the study with the other two patients reporting maintenance of the improvement in smell acuity previously achieved with oral theophylline.

Discussion

Preliminary results of this trial of intranasal theophylline indicate that patients can administer the drug without difficulty. Further, no side effects were observed with the intranasal administration of theophylline. Additionally, all of the patients preferred intranasal administration over oral administration with six of the eight evaluable patients studied noting significant improvement in taste and smell function after use of intranasal over that achieved with oral theophylline. All ten patients reported no diminution of their smell function using intranasal administration demonstrating that they are receiving at least an equivalent dose of theophylline by intranasal administration. As the last two patients have not yet completed the study, the number of patients responding to the intranasal therapy may further increase. Furthermore, taste and smell acuity was stable or improved without producing measureable blood theophylline levels.

One of the patients that achieved an improved sense of smell did not wish to return the unused portion of the intranasal theophylline since the methodology also successfully enhanced her nasal breathing, nasal homeostasis and ability to sleep more soundly at night due to improvement in nasal function.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating anosmia or hyposmia in a human in need thereof, the method comprising: administering to the human in need thereof, a steroid-free pharmaceutical dosage unit for intranasal administration comprising an effective amount of theophylline, wherein the steroid-free pharmaceutical dosage unit comprises less than 1 mg of theophylline and a pharmaceutically acceptable carrier.

2. The method of claim 1, wherein the dosage unit comprises less than 500 µg, less than 250 µg, or less than 100 µg of the theophylline.

3. The method of claim 1, wherein the dosage unit is formulated as a liquid or dry powder.

4. The method of claim 1, wherein the dosage unit is administered at least once, twice, or thrice daily.

5. The method of claim 1, wherein successful treatment comprises an increase in taste or smell acuity of at least 5%.

6. The method of claim 5, wherein the increase in taste or smell acuity is accompanied by an increase in nasal mucus or saliva cAMP or cGMP levels.

7. A steroid-free pharmaceutical dosage unit for intranasal administration comprising an amount of theophylline effective for treating anosmia or hyposmia in a human in need thereof, wherein the steroid-free pharmaceutical dosage unit comprises less than 1 mg of the theophylline and a pharmaceutically acceptable carrier.

8. The dosage unit of claim 7, that is a dry powder.

9. The dosage unit of claim 7, that is a liquid.

10. The dosage unit of claim 7, further comprising an excipient.

11. The dosage unit of claim 7, wherein the pH of the dosage unit is from 5.5-7.5.

12. The dosage unit of claim 7, that comprises less than 500 µg, less than 250 µg, or less than 100 µg of the theophylline.

13. The dosage unit of claim 7, that comprises about 40 µg of the theophylline.

14. The dosage unit of claim 7, that comprises about 20 µg of the theophylline.

15. The dosage unit of claim 10, wherein the excipient is methylparaben and/or propylparaben.

16. The dosage unit of claim 9, wherein the volume of the dosage unit is about 0.4 mL.

17. The dosage unit of any one of claim 7, 8, or 9, having a theophylline unit dose from about 0.001 µg/kg to about 10.0 µg/kg of body weight per day.

* * * * *

UNITED STATES PATENT AND TRADEMARK OFFICE
CERTIFICATE OF CORRECTION

| | | |
|---|---|---|
| PATENT NO. | : 8,580,801 B2 | Page 1 of 1 |
| APPLICATION NO. | : 12/508530 | |
| DATED | : November 12, 2013 | |
| INVENTOR(S) | : Robert I. Henkin | |

It is certified that error appears in the above-identified patent and that said Letters Patent is hereby corrected as shown below:

In the Claims

COLUMN 46, LINE 39:

"claim" should read -- claims --

Signed and Sealed this
Third Day of June, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,580,801 B2 | Page 1 of 1 |
| APPLICATION NO. | : 12/508530 | |
| DATED | : November 12, 2013 | |
| INVENTOR(S) | : Robert I. Henkin | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 640 days.

Signed and Sealed this
Ninth Day of June, 2015

Michelle K. Lee
*Director of the United States Patent and Trademark Office*